(12) United States Patent
Hsieh et al.

(10) Patent No.: US 10,835,493 B2
(45) Date of Patent: Nov. 17, 2020

(54) PLATELET-LIKE PROTEO-MICROPARTICLES AND METHOD OF USING SUCH IN DRUG DELIVERY

(71) Applicant: Academia Sinica, Taipei (TW)

(72) Inventors: Patrick C. H. Hsieh, Taipei (TW); Bill Cheng, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 15/567,837

(22) PCT Filed: Apr. 20, 2016

(86) PCT No.: PCT/AU2016/000135
§ 371 (c)(1),
(2) Date: Oct. 19, 2017

(87) PCT Pub. No.: WO2016/168884
PCT Pub. Date: Oct. 27, 2016

(65) Prior Publication Data
US 2018/0092846 A1    Apr. 5, 2018

Related U.S. Application Data

(60) Provisional application No. 62/149,849, filed on Apr. 20, 2015.

(51) Int. Cl.
*A61K 9/127*    (2006.01)
*A61K 9/50*    (2006.01)
(Continued)

(52) U.S. Cl.
CPC .......... *A61K 9/1271* (2013.01); *A61K 9/0019* (2013.01); *A61K 9/1277* (2013.01);
(Continued)

(58) Field of Classification Search
None
See application file for complete search history.

(56) References Cited

U.S. PATENT DOCUMENTS 5,238,919 A * 8/1993 Zimmerman ........ C07K 14/755
514/13.7
5,503,982 A * 4/1996 Hendricks ........ G01N 33/56966
422/82.02

(Continued)

FOREIGN PATENT DOCUMENTS

CN    1596910 A    3/2005
EP    0894807 A1    2/1999
(Continued)

OTHER PUBLICATIONS

C Kelly, C Jeffries, S-A Cryan. "Targeted Liposomal Drug Delivery to Monocytes and Macrophages." Journal of Drug Delivery, vol. 2011, Article ID 727241, pp. 1-11. (Year: 2011).*
(Continued)

*Primary Examiner* — Isaac Shomer
(74) *Attorney, Agent, or Firm* — Polsinelli PC; Tara A. Nealey; Ron Galant

(57) ABSTRACT

Proteo-microparticles such as proteoliposomes comprising a microparticle (e.g., a liposome) and platelet membrane proteins, wherein the proteo-microparticles are capable of binding to monocytes, neutrophils, or other circulating blood cells capable of migrating to an injured site. Also provided herein are uses of the proteoliposomes for delivering a therapeutic agent via monocytes to an injured site.

12 Claims, 23 Drawing Sheets
Specification includes a Sequence Listing.

(51) Int. Cl.
 A61K 31/409 (2006.01)
 A61K 9/00 (2006.01)
 A61K 31/555 (2006.01)
(52) U.S. Cl.
 CPC .......... *A61K 31/409* (2013.01); *A61K 31/555* (2013.01); *A61K 9/5068* (2013.01)

(56) References Cited

U.S. PATENT DOCUMENTS

| | | | |
|---|---|---|---|
| 6,177,059 B1* | 1/2001 | Matsuda | A61K 9/1271 424/1.21 |
| 2010/0008937 A1* | 1/2010 | Peer | C12N 15/111 514/1.1 |
| 2010/0151573 A1 | 6/2010 | King et al. | |
| 2014/0023591 A1 | 1/2014 | Sen Gupta et al. | |
| 2014/0099359 A1* | 4/2014 | Sen Gupta | A61K 9/1271 424/450 |
| 2014/0186431 A1 | 7/2014 | Wang et al. | |

FOREIGN PATENT DOCUMENTS

| | | |
|---|---|---|
| JP | 2007-204469 A | 8/2007 |
| JP | 2010-534193 A | 11/2010 |

OTHER PUBLICATIONS

E Karathanasis, CM Geigerman, CA Parkos, L Chan, RV Bellamkonda, DL Jaye. "Selective Targeting of Nanocarriers to Neutrophils and Monocytes." Annals of Biomedical Engineering, vol. 37 No. 10, Oct. 2009, pp. 1984-1992. (Year: 2009).*
J Li, K Kim, A Barazia, A Tseng, J Cho. "Platelet-neutrophil interactions under thromboinflammatory conditions." Cellular and Molecular Life Sciences, vol. 72, 2015, pp. 2627-2643. Available online Feb. 4, 2015. (Year: 2015).*
JE Willard, RA Lange, LD Hillis. "The Use of Aspirin in Ischemic Heart Disease." The New England Journal of Medicine, vol. 327, No. 3, Jul. 16, 1992, pp. 175-181. (Year: 1992).*
DI Siegel-Axel, M Gawaz. "Platelets and Endothelial Cells." Seminars in Thrombosis and Hemostasis, vol. 33 No. 2, 2007, pp. 128-135. (Year: 2007).*
V Leytin et al. "Flow Cytometric Parameters for Characterizing Platelet Activation by Measuring P-Selectin (CD62) Expression: Theoretical Consideration and Evaluation in Thrombin-Treated Platelet Populations." Biochemical and Biophysical Rsearch Communications, vol. 269, 2000, pp. 85-90. (Year: 2000).*
J Graff et al. "Close Relationship between the Platelet Activation Marker CD62 and the Granular Release of Platelet-Derived Growth Factor." The Journal of Pharmacology and Experimental Therapeutics, vol. 300 No. 3, 2001, pp. 952-957. (Year: 2001).*
A Matzdorff, R Voss. "Upregulation of GP IIb/IIIa receptors during platelet activation: Influence on efficacy of receptor blockade." Thrombosis Research, vol. 117, 2006, pp. 307-314. (Year: 2006).*
TG Diacovo, SJ Roth, JM Buccola, DF Bainton, TA Springer. "Neutrophil Rolling, Arrest, and Transmigration Across Activated, Surface-Adherent Platelets Via Sequential Action of P-Selectin and the b2-Integrin CD11b/CD18." Blood, vol. 88 No. 1, Jul. 1996, pp. 146-157. (Year: 1996).*
P Andre, L Nannizzi-Alaimo, SK Prasad, DR Phillips. "Platelet-Derived CD40L The Switch-Hitting Player of Cardiovascular Disease." Circulation, vol. 106, 2002, pp. 896-899. (Year: 2002).*
MEM Rybak, LA Renzulli. "A Liposome Based Platelet Substitute, The Plateletsome, with Hemostatic Efficacy." Biomaterials, Artificial Cells, & Immobilization Biotechnology, vol. 21(2), 1993, p. 101-118. (Year: 1993).*
S-H Yun, E-H Sim, R-Y Goh, J-I Park, J-Y Han. "Platelet Activation: The Mechanisms and Potential Biomarkers." Hindawi Publishing Corporation BioMed Research International, vol. 2016, Article ID 9060143, pp. 1-5, published in 2016. (Year: 2016).*

AK Litvinenko et al. "Fluorescence-Free Flow Cytometry for Measurement of Shape Index Distribution of Resting, Partially Activated, and Fully Activated Platelets." Cytometry Part A, vol. 89A, 2016, pp. 1010-1016, published Oct. 21, 2016. (Year: 2016).*
ML Nierodzik, S Karpatkin. "Thrombin induces tumor growth, metastasis, and angiogenesis: Evidence for a thrombin-regulated dormant tumor phenotype." Cancer Cell, vol. 10, Nov. 2006, pp. 355-362. (Year: 2006).*
JE Freeman. "CD40-CD40L and Platelet Function Beyond Hemostasis." Circulation Research, vol. 92, 2003, pp. 944-946. (Year: 2003).*
R&D Systems Catalog. "Adhesion Molecules I." https://www.rndsystems.com/resources/articles/adhesion-molecules-i downloaded from web Jan. 15, 2020, first published in R&D Systems' 1996 Catalog, 3 printed pages. (Year: 1996).*
M Merten, P Thiagarajan. "P-Selectin Expression on Platelets Determines Size and Stability of Platelet Aggregates." Circulation, vol. 102, 2000, pp. 1931-1936. (Year: 2000).*
KK Brown, PM Henson, J Maclouf, M Moyle, JA Ely, GS Worthen. "Neutrophil-Platelet Adhesion: Relative Roles of Platelet P-Selectin and Neutrophil b2 (CD18) Integrins." American Journal of Respiratory Cell and Molecular Biology, vol. 18, 1998, pp. 100-110. (Year: 1998).*
P Rozman. "Platelet antigens. The role of human platelet alloantigens (HPA) in blood transfusion and transplantation." Transplant Immunology, vol. 10, 2002, pp. 165-181. (Year: 2002).*
HM Rinder, JL Bonan, CS Rinder, KA Ault, BR Smith. "Activated and Unactivated Platelet Adhesion to Monocytes and Neutrophils." Blood, vol. 78 No. 7, Oct. 1991, pp. 1760-1769. (Year: 1991).*
Valerie B. O'Donnell, Robert C. Murphy, Steve P. Watson. "Platelet Lipidomics Modern Day Perspective on Lipid Discovery and Characterization in Platelets." Circulation Research, vol. 114, 2014, pp. 1185-1203. (Year: 2014).*
Sarah C Lee, et al. "A method for detergent-free isolation of membrane proteins in their local lipid environment." Nature Protocols, vol. 11 No. 7, 2016, pp. 1149-1162. (Year: 2016).*
Baldassare et al., Reconstruction of platelet proteins into phospholipid vesicles. Functional proteoliposomes. J Clin Invest. Jan. 1985;75(1):35-9.
Cheng et al., Platelet-like proteoliposomes enable active drug delivery to infarcted heart tissue. Front. Bioeng. Biotechnol. Conference Abstract: 10th World Biomaterials Congress. Mar. 30, 2016.
Dalencon et al., Liposomes bearing platelet proteins: a model for surface functions studies. Biochim Biophys Acta. Aug. 16, 1996;1302(3):241-8.
Hu et al., Anticancer Platelet-Mimicking Nanovehicles. Adv Mater. Nov. 25, 2015;27(44):7043-50. doi: 10.1002/adma.201503323. Epub Sep. 29, 2015.
Hu et al., Nanoparticle biointerfacing by platelet membrane cloaking. Nature. Oct. 1, 2015;526(7571):118-21. doi: 10.1038/nature15373. Epub Sep. 16, 2015.
Lecoanet-Henchoz et al., CD23 regulates monocyte activation through a novel interaction with the adhesion molecules CD11b-CD18 and CD11c-CD18. Immunity. 1995;3:119-125.
Li et al., Targeted drug delivery to circulating tumor cells via platelet membrane-functionalized particles. Biomaterials. Jan. 2016;76:52-65. doi:10.1016/j.biomaterials.2015.10.046. Epub Oct. 21, 2015.
Nishiya et al., Reconstitution of adhesive properties of human platelets in liposomes carrying both recombinant glycoproteins Ia/IIa and Ib alpha under flow conditions: specific synergy of receptor-ligand interactions. Blood. Jul. 1, 2002;100(1):136-42.
Sloan et al., Glycoprotein IIb-IIIa-liposomes bind fibrinogen but do not undergo fibrinogen-mediated aggregation. Platelets. Mar. 2000;11(2):99-110.
Extended European Search Report dated Oct. 24, 2018 in connection with EP16/782,388.9.
Hamori et al. Targeting zinc protoporphyrin liposomes to the spleen using reticuloendothelial blockade with blank liposomes. Pediatr Res. Jul. 1993;34(1):1-5.
Jang et al. Syndecan-4 proteoliposomes enhance fibroblast growth factor-2 (FGF-2)-induced proliferation, migration, and neovasculariza-

(56) References Cited

OTHER PUBLICATIONS tion of ischemic muscle. Proc Natl Acad Sci U S A. Jan. 31, 2012;109 (5):1679-84. doi: 10.1073/pnas.1117885109. Epub Jan. 17, 2012.

Jopski, Bettina, et al.; "Preparation of hemoglobin-containing liposomes using octyl glucoside and octyltetraoxyethylene"; Elsevier Science Publishers B.V.; Jul. 5, 1988; pp. 79-84.

Sloan, Stephen Michael, Glycoprotein IIB-IIIa-Liposomes Bind Fibrinogen But Do Not Undergo Fibrinogen-Mediated Aggregation, National Library of Canada, 1997, p. i-viii, 1-127 (cited to indicate well-known technology).

\* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
gagcagaacc agcctgaact        20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
tttgaacttg gtggggctgt        20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
tagcccacgt cgtagcaaac        20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
accctgagcc ataatcccct        20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
gatgcagtta acgccccact        20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
acccattcct tcttggggtc        20

<210> SEQ ID NO 7
<211> LENGTH: 21
<212> TYPE: DNA
<213> ORGANISM: Artificial Sequence

```
<220> FEATURE:
<223> OTHER INFORMATION: Synthetic polynucleotide

<400> SEQUENCE: 7
tgccaccttt tgacagtgat g                                          21

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
ttcttgtgac cctgagcgac                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
gccttcttgg gactgatgct                                            20

<210> SEQ ID NO 10
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 10
tggaaattgg ggtaggaagg ac                                         22
```

PLATELET-LIKE PROTEO-MICROPARTICLES AND METHOD OF USING SUCH IN DRUG DELIVERY

CROSS-REFERENCE TO RELATED APPLICATION

This application is a national stage filing under 35 U.S.C. § 371 of International Application No. PCT/AU2016/000135, entitled "PLATELET-LIKE PROTEO-MICROPARTICLES AND METHOD OF USING SUCH IN DRUG DELIVERY", filed Apr. 20, 2016, which claims the benefit of the filing date of U.S. Provisional Application No. 62/149,849, entitled "PLATELET-LIKE PROTEO-MICROPARTICLES AND METHOD OF USING SUCH IN DRUG DELIVERY," filed Apr. 20, 2015, the contents of each of which are incorporated herein by reference herein in their entirety.

BACKGROUND OF THE INVENTION

Chronic diseases such as cancers and ischemic heart diseases continue to be the major causes of deaths in many countries. Bauer et al., (2014), The Lancet 384:45-52. Not only these diseases represent a huge portion on many countries' annual healthcare budget, but also create irreplaceable costs on affected families both financially and emotionally. Although, a continuous advancement has been made in developing novel therapeutics and identifying new potential drug targets for many chronic diseases, the therapeutic applications of these potential treatments are still limited. One of the key challenges that many treatments face today is targeting specificity: how to restrict the therapeutic actions at the targeted site only. Raj et al., (2014), Drug Delivery 2014:1-20.

Over past decades, a continued advancement has been made in identifying and developing new drug targets for ischemic heart diseases (IHD). However, IHD continues to be the major cause of death in many countries. Go et al., (2014), Circulation 129:e28-e292. It is now well-established that the actions of most of these treatments are often not restricted to the targeted site. Vander Heide et al., (2013) Circulation Res 113:464-477. Thus, how to successfully delivered a well-established therapeutic to the site of interest is still a major challenge that remains to be met.

One of the key events that happen during the development of IHD is the recruitment of circulating monocytes to the infarct area. Liu et al., (2011), Arterioscler Thromb Vasc Biol 31:834-841; Sarma et al., (2002), Circulation 105:2166-2171; Furman et al., (2001), J Am Coll Cardiol 38:1002-1006. Once these circulating monocytes cross the endothelial lining they becomes macrophages, which then causes more damage to the infarct heart through their inflammatory activity. Although therapeutics have been developed to target these macrophages, studies have shown the action of these therapeutics not only affects the macrophages at the infarct heart area but also those elsewhere in the body. Ley et al., (2011), Arterioscler Thromb Vasc Biol 31:1506-1516.

SUMMARY OF THE INVENTION

The present disclosure is based on the design of proteoliposomes comprising a liposome and platelet membrane proteins. Such proteoliposomes are capable of binding to circulating blood cells such as monocytes but not endothelial cells. As such, these proteoliposomes can be used for delivering a therapeutic agent encapsulated thereof via binding to monocytes, which are capable of migrating to an injured site, for example, a heart infarct area. Once the monocytes develop into macrophages, the proteoliposomes may be absorbed by the macrophages via endocytosis, thereby delivering the therapeutic agent to a site where monocytes accumulates, such as an infarct area. Alternatively, the therapeutic agent can be released at a diseased site where the monocytes or macrophages accumulate prior to endocytosis of the proteoliposomes.

Accordingly, the present disclosure provides a proteo-microparticle such as proteoliposome comprising a microparticle (e.g., a liposome) and one or more platelet membrane proteins, wherein the proteoliposome binds monocytes, neutrophiles, or other circulating cells, which can migrate to an injured site either passively or actively. In some embodiments, the proteo-microparticle encapsulates a therapeutic agent, such as a cardio-protective agent, for example, an anti-inflammatory agent, an anti-apoptotic agent, an anti-fibrotic agent, an immuno-modulatory agent, or a proangiogenic agent. In some embodiments, the liposome comprises a phospholipid and cholesterol.

In any of the proteo-microparticles such as proteoliposomes described herein, the one or more platelet membrane proteins may comprise a protein mixture isolated from membranes of platelets. In some embodiments, the platelets are resting platelets or partially activated platelets. As used herein, partially activated platelets refer to platelets that express early stage activation markets such as CD62P but not fully activation markers such as CD40L and CD18.

In some embodiments, the proteo-particles such as proteoliposomes described herein are substantially free of lipid components of platelet membranes. Alternatively or in addition, any of the proteo-microparticles (e.g., proteoliposomes) described herein does not bind endothelial cells.

In another aspect, the present disclosure provides a method for delivering a therapeutic agent to a subject, comprising administering to the subject any of the proteo-microparticles (e.g., any of the proteoliposomes) described herein, which encapsulates the therapeutic agent.

In yet another aspect, the present disclosure provides a method for treating an ischemic heart disease, comprising administering to a subject in need thereof an effective amount of any of the proteo-microparticles (e.g., proteoliposomes) described herein, which encapsulat a therapeutic agent for treating the ischemic heart disease (IHD). In some embodiments, the anti-IHD agent is an anti-inflammatory agent.

Also within the scope of the present disclosure are (a) a pharmaceutical composition for use in delivering a therapeutic agent to a target site (e.g., an injured site) or for use in treating an IHD, the pharmaceutical composition comprising any of the proteo-microparticle (e.g., proteoliposomes) described herein, which encapsulates a therapeutic agent such as an anti-IHD agent (e.g., an anti-inflammatory agent) and a pharmaceutically acceptable carrier, and (b) uses of the proteoliposome as described herein in manufacturing a medicament for delivering a therapeutic agent to a target site or for use in treating an IHD.

Further, the present disclosure provides a kit for drug delivery, the kit comprising any of the proteo-microparticles described herein and a therapeutic agent such as those described herein. The therapeutic agent is encapsulated by the proteo-microparticle.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

FIG. 1A is a schematic illustration showing the fabrication of PLPs, comprising conjugating purified human platelet membrane proteins (PMPs) with DOPC-based liposomes by the thin-film hydration method. FIG. 1B is a schematic illustration showing the overall strategy. Platelets adhere to the surfaces of recruited monocytes during the development of myocardial infarction (see 1). Accordingly, the platelet monocyte aggregates undergo extravasation (see 2). Thus, platelet-like proteoliposomes (PLPs) would interact with monocytes in a similar way to platelets (see 3). Once crossing the endothelium, the PLPs would be phagocytized by monocyte-derived macrophages (see 4). FIG. 1C shows PMPs purified from freshly isolated human platelets after rounds of ultra-centrifugation steps. FIG. 1D is a photo demonstrating the purity of the membrane proteins as determined by SDS-PAGE. The black box indicates that β-actin (black box) was not visible in the final purified membrane protein solution. The white box show protein bands obtained from the final membrane protein solution. FIG. 1E is a diagram showing the identities of some of the platelet membrane proteins as determined by Western blotting. FIG. 1F includes photos showing cryo-EM images of plain liposomes (without PMPs conjugations) and PLPs; scale bar, 100 μm. FIG. 1G is a photo showing presence of GPIIb and CD42c in various samples as indicated. 10 mg/mL of PLPs were concentrated down to 1 mg/mL by ultracentrifugation, and PMPs conjugated to PLPs were identified by Western blotting using the anti-GPIIb and anti-CD42c antibodies.

FIG. 2A shows fluorescent images of platelet-like proteoliposomes interacting with different cell types compared to liposomes. FIG. 2B presents flow cytometric analysis of platelet-like proteoliposomes bound to different cell types.

FIG. 5C shows the localization of either DiI-labeled liposomes or PLPs in I/R injured hearts was analyzed on the frozen-sectioned samples (nucleus, blue; troponin I, green). FIG. 5D shows flow cytometry and statistical analysis of CD11b$^+$ (FIG. 5E) and CD11b$^+$DiI$^+$ (FIG. 5F) non-myocyte cells isolated from I/R injured murine hearts after 4 hours of exposure to either plain liposomes or PLPs injected at 24 or 72 hours of reperfusion. n=5, *, P<0.001.

FIG. 6A shows the study protocol: the mice were subjected to 45 minutes of ischemia and 72 hours of reperfusion, followed by intravenous injection of saline, CoPP (5 mg/Kg), Lipo–CoPP (5 mg/Kg) or PLP–CoPP (5 mg/Kg). Subsequent injections were made every 5 days until day 28, at which point the mice were sacrificed. Subsequently, the heart tissues of the mice were sectioned and stained with Masson's trichrome (FIG. 6B). NT; not treated, CoPP; free CoPP, Lipo+CoPP; liposome-encapsulated CoPP, PLP+CoPP; PLP-encapsulated CoPP. Scale bar; 1 mm for the whole section and 100 μm for the higher magnified images. FIG. 6C shows statistical analysis of the infarct area of the hearts in each treatment group (n=4), *, P<0.05; n.s., not significant. FIG. 6D shows expressions of HO-1 genes and the pro-inflammatory genes detected in the I/R injured hearts after i.v. injections of different treatments at 72 hours of reperfusion.

FIG. 7A shows the treatment protocol: after permanent ligation was performed on the LAD artery, the mice were allowed to rest for 72 hours before being intravenously injected with ~100 μL of saline, Lipo-only, PLPs-only, CoPP (5 mg/Kg), Lipo–CoPP (5 mg/Kg) or PLP–CoPP (5 mg/Kg). Treatments were then given every 5 days until day 28, at which point the cardiac function of the mice was assessed by echocardiography (n=8) (FIG. 7B); LVEF, left ventricular ejection fraction; FS, fraction shortening; LVEDV, left ventricular end-diastolic volume; LVESV, left ventricular end-systolic volume; IVSd, interventricular septal thickness at diastole; IVSs, interventricular septal thickness at systole. The blood of the mice was analyzed for biomarkers to assess liver function (FIG. 7C), renal function (FIG. 7D), and cardiac function (FIG. 7E); AST, aspartate aminotransferase; ALT, alanine aminotransferase; TBIL, total bilirubin; BUN, blood urea nitrogen; CRE, creatinine; CKMB, creatine kinase MB, *, P<0.05, ***, P<0.001.

FIG. 10A is a schematic diagram showing the relationship between CoPP, HO-1 and bilirubin. Cells were exposed to either liposome or PLPs at 37° C. for 4 hours; any excess was rinsed off with PBS. The cells were then placed back in a 37° C. incubator overnight before subjecting to western blotting (FIG. 10B). FIG. 10C presents the specific activity of the induced HO-1 in every treated sample, in catalyzing heme into bilirubin (n=6). NT; not treated, CoPP; free CoPP, Lipo+CoPP; liposome-encapsulated CoPP, PLP+CoPP; PLP-encapsulated CoPP. *, P<0.05, ***, P<0.001.

DETAILED DESCRIPTION OF THE INVENTION

Figure 1A:
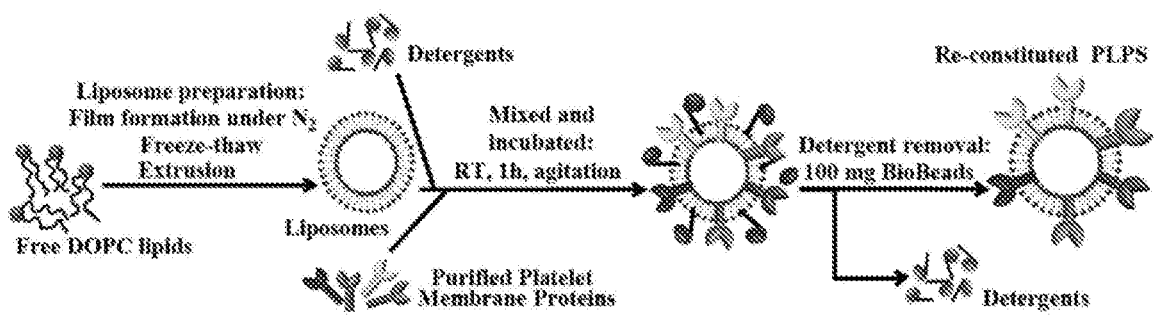
FIGS. 1A-1G show human PMPs purification and PLPs fabrication.

The recruitment of macrophages to a disease site is a key event that happens during pathogenesis inpatients with acute or chronic diseases. Pawelec et al., Current opinion in immunology. 2014; 29:23-28. These macrophages first appear as monocytes in blood vessels. Gordon et al., Nature Reviews Immunology. 2005; 5:953-964. The circulating monocytes would then travel to the vessel that closest to the disease site, and then reach the site by penetrating through the endothelial lining, a process known as extravasation. Hume, Current opinion in immunology. 2006; 18:49-53.

The present disclosure provides a platelet-like proteo-microparticle such as proteoliposome (PLP) that is capable of binding to monocytes and thus is useful in delivering agents such as diagnostic or therapeutic agent to a desired site, e.g., a site where disease occurs, via migration of the monocytes. A proteo-microparticle is a microparticle (e.g. a nanoparticle) that comprises one or more proteins, which preferably are displayed on the surface of the microparticle. The PLP described herein is a liposome-based delivery system with purified platelet membrane proteins on its surfaces. Such PLPs may serve as an advantageous drug delivery vehicle, which is capable of using the circulating blood cells such as monocytes as a 'shuttle' to allow a therapeutic agent encapsulated by the PLP to reach a target site of interest, such as an infarct heart area. Once the circulating monocytes that carry the PLP cross the endothelial lining, they would be activated to form macrophages. Subsequently, these self-activated macrophages would phagocytize the surface-bound PLP, allowing the encapsulated drugs (e.g., anti-inflammatory agent) to release or function inside the macrophages, thereby exerting its therapeutic effect. In some instances, the drug can function to change the gene expression profile of the macrophages, which uptake the PLPs, leading to the reduction of cytokine/chemokine excretion and/or enhancing secretion of favourable factors to promote tissue repair/regeneration.

Without being bound by theory, the PLP described herein may confer the following benefits. First, it provides a new approach for delivering a therapeutic agent to a target site of interest, such as an infarct heart area, for treating a target disease such as IHD. Second, in some preferred embodiments, the PLP described herein comprises only membrane proteins from resting or partially (weakly) activated platelets. Such a PLP does not bind to endothelial cells and thus would not cause undesirable thrombosis.

Platelet-Like Proteo-Microparticles

The proteo-microparticles described herein can be any microparticle that comprises one or more platelet membrane proteins, which may be displayed on the surface of the microparticle. In some embodiments, the proteo-microparticles described herein are platelet-like proteoliposomes (PLPs), which refers to liposome-like vehicles having one or more platelet membrane proteins inserted, usually by artificial means, into the membrane of the liposome. The PLP may comprise a liposome, in which one or more platelet membrane proteins are inserted. At least a portion of the platelet membrane protein(s) may be exposed on the surface of the PLPs such that the protein can interact with a binding partner, for example, a receptor on the surface of a circulating blood cells such as a monocyte. In some embodiments, the ratio between the lipids in the liposome and the platelet membrane protein(s) ranges from 1,000,000:1 to 30:1 (w/w). In some examples, the ratio is 1,000:1, 30:1 to 50:1 (w/w), e.g., 30:1 to 40:1 or 40:1 to 50:1.

The PLPs described herein are capable of binding to monocytes, neutrophils, and/or other circulating blood cells that could migrate to an injured site. In some embodiments, the PLPs specifically bind to monocytes as relative to other types of cells such as endothelial cells. A PLP that "specifically binds" to a target cell such as monocyte is a term well understood in the art, and methods to determine such specific binding are also well known in the art. A PLP is said to exhibit "specific binding" activity to a target cell such as monocyte if it reacts or associates more frequently, more rapidly, with greater duration and/or with greater affinity with the target cell than it does with alternative target cells (e.g., endothelial cells). A PLP "specifically binds" to monocytes if it binds with greater affinity, avidity, more readily, and/or with greater duration than it binds to other types of cells such as endothelial cells. It is also understood by reading this definition that, for example, a PLP that specifically binds to a first target cell may or may not specifically or preferentially bind to a second target cell. As such, "specific binding" or "preferential binding" does not necessarily require (although it can include) exclusive binding. Generally, but not necessarily, reference to binding means preferential binding. In some specific examples, the PLP described herein does not bind to endothelial cells and thus does no induce thrombosis, i.e., the PLP binds to endothelial cells at no or a substantially low level such that the binding, if any, is not sufficient to induce significant thrombosis (e.g., clinical meaningful thrombosis, which can be determined by routine medical assays).

In some embodiments, the PLPs described herein are substantially free of lipid components of platelet membranes (the whole or a portion thereof). By "substantially free," it means that the PLPs contain no more than a minimum amount of platelet membranes, e.g., less than about 10%, less than about 5%, or less than about 2.5% platelet membranes. In some examples, the PLPs contains no lipid components of platelet membranes (i.e., free of lipid components of platelet membranes).

(i) Liposomes and Other Microparticles

The term "liposome" as used herein, refers to a composition comprising an outer lipid layer membrane (e.g., a single lipid bi-layer known as unilamellar liposomes or multiple lipid bi-layers known as multilamellar liposomes) surrounding an internal aqueous space. See. e.g., Cullis et al., Biochim. Biophys Acta, 559:399-420 (1987). A unilamellar liposome generally has a diameter in the range of about 20 to about 400 nanometers (nm), about 50 to about 300 nm, about 300 to about 400 nm, or about 100 to about 200 nm. A multilamellar liposome usually has a diameter in the range of about one to about ten micrometers and may comprise anywhere from two to hundreds of concentric lipid bilayers alternating with layers of an aqueous phase.

Each of the lipid bi-layers may comprise two monolayers containing oppositely oriented amphipathic lipid molecules. Amphipathic lipids typically comprise a polar (hydrophilic) headgroup covalently linked to one or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups are oriented towards the bilayer's surface and acyl chains are oriented towards the interior of the bilayer, effectively shielding the acyl chains from contact with the aqueous environment.

One or more naturally occurring and/or synthetic lipid compounds may be used in the preparation of the liposomes described herein. The liposomes may contain negatively charged lipids, positively charged lipids, or a combination thereof. Examples of suitable negatively charged lipids include, but are not limited to dimyrystoyl, -dipalmitoyl- and distearoylphasphatidylglycerol, dimyrystoyl, -dipalmitoyl- and dipalmitoylphosphatidic acid, dimyrystoyl, -dipalmitoyl- and dipalmitoylphosphatidylethanolamine, their unsaturated diacyl and mixed acyl chain counterparts as well as cardiolipin. Examples of positively charged lipids include, but are not limited to, N,N'-dimethyl-N,N'-dioctacyl ammonium bromide (DDAB) and chloride DDAC), N-(1-(2,3-dioleyloxy)propyl)-N,N,N-trimethylammonium chloride (DOTMA), 3.beta.-[N—(N',N'-dimethylaminoethyl) carbamoyl] cholesterol (DC-chol), 1,2-dioleoyloxy-3-[trimethylammonio]-propane (DOTAP), 1,2-dioctadecyloxy-3-[trimethylammonio]-propane (DSTAP), and 1,2-dioleoyloxypropyl-3-dimethyl-hydroxyethyl ammonium chloride (DORI) and cationic lipids described in e.g. Martin et al., Current Pharmaceutical Design 2005, 11, 375-394.

In some embodiments, the liposome described herein can be prepared using one or more phospholipids, and optionally one or more additional molecules of similar molecular shape and dimensions having both a hydrophobic moiety and a hydrophilic moiety (e.g., cholesterol). Suitable phospholipids for use in preparing the liposomes described herein include, but are not limited to, phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol. Additional nonphosphorous-containing lipids include, but are not limited to, stearyl amine, dodecylamine/hexadecyl-amine, acetyl, palmitate, glycerol, ricinoleate, hexadecyl sterate, isopropyl myristate, amphoteric acrylic polymers, fatty acid, fatty acid amides, cholesterol, cholesterol ester, diacylglycerol, diacylglycerolsuccinate, and the like.

In some embodiments, the major lipid component of the liposomes described herein can be phosphatidylcholine, which may have a variety of acyl chain groups of varying chain length and degree of saturation. In some examples, the phosphatidylcholines contain saturated fatty acids with carbon chain lengths in the range of, e.g., $C_{14}$ to $C_{22}$. Saturated long-chain phosphatidylcholines are less permeable and more stable in vivo than their unsaturated counterparts. Phosphatidylcholines with mono- or di-unsaturated fatty acids and mixtures of saturated and unsaturated fatty acids may also be used.

Any of the liposomes described herein may further comprise a sterol, preferably cholesterol, at molar ratios ranging from about 0.1 to 1.0 (cholesterol:phospholipid). In some examples, the liposomes may comprise a combination of distearoylphosphatidylcholine/cholesterol, dipalmitoylphosphatidylcholin/cholesterol, dimyrystoylphosphatidylcholine/cholesterol, 1,2-Dioleoyl-sn-glycero-3-phosphocholine (DOPC)/cholesterol, or egg sphingomyelin/cholesterol.

When needed, the liposomes described herein may be coated with a polymer layer to enhance stability of the liposomes in vivo (e.g., sterically stabilized liposomes). Examples of suitable polymers include, but are not limited to, poly(ethylene glycol), which may form a hydrophilic surface layer that improves the circulation half-life of liposomes and enhances the amount of liposomes that reach therapeutic targets. See, e.g., Working et al. J Pharmacol Exp Ther, 289: 1128-1133 (1999); Gabizon et al., J Controlled Release 53: 275-279 (1998); AdlakhaHutcheon et al., Nat Biotechnol 17: 775-779 (1999); and Koning et al., Biochim Biophys Acta 1420: 153-167 (1999). Examples of useful PEG-lipids for use in making the liposomes described herein include, but are not limited to, 1,2-diacyl-sn-Glycero-3-Phosphoethanolamine-N-[Methoxy(Polyethylene glycol)-350] (mPEG 350 PE); 1,2-Diacyl-sn-Glycero-3-Phosphoethanolamine-N-[Methoxy(Polyethylene glycol)-550] (mPEG 550 PE); 1,2-Diacyl-sn-Glycero-3-Phosphoethanolamine-N-[Methoxy(Polyethylene glycol)-750] (mPEG 750 PE); 1,2-Diacyl-sn-Glycero-3-Phosphoethanolamine-N-[Methoxy(Polyethylene glycol)-1000] (mPEG 1000 PE); 1,2-Diacyl-sn-Glycero-3-Phosphoethanolamine-N-[Methoxy(Polyethylene glycol)-2000] (mPEG 2000 PE); 1,2-Diacyl-sn-Glycero-3-Phosphoethanolamine-N-[Methoxy(Polyethylene glycol)-3000] (mPEG 3000 PE); 1,2-Diacyl-sn-Glycero-3-Phosphoethanolamine-N-[Methoxy(Polyethylene glycol)-5000] (mPEG 5000 PE); N-Acyl-Sphingosine-1-[Succinyl(Methoxy Polyethylene Glycol) 750] (mPEG 750 Ceramide); N-Acyl-Sphingosine-1-[Succinyl(Methoxy Polyethylene Glycol) 2000] (mPEG 2000 Ceramide); and N-Acyl-Sphingosine-1-[Succinyl (Methoxy Polyethylene Glycol) 5000] (mPEG 5000 Ceramide).

A variety of methods can be used for preparing the liposomes described herein. Such methods are known in the art or disclosed herein, for example, the methods described in Lichtenberg and Barenholz in Methods of Biochemical Analysis, Volume 33, 337-462 (1988). See also Szoka et al., Ann. Rev. Biophys. Bioeng. 9:467 (1980); U.S. Pat. Nos. 4,235,871, 4,501,728, and 4,837,028; Liposomes, Marc J. Ostro, ed., Marcel Dekker, Inc., Hew York, 1983, Chapter 1; and Hope, et al., Chem. Phys. Lip. 40:89 (1986), the relevant disclosures of each of which are incorporated herein by reference. Small unilamellar vesicles (SUV, size <100 nm)

can be prepared by a combination of standard methods of thin-film hydration and repeated extrusion as described before (Tseng et al., 1999).

Conventional techniques are available for sizing liposomes to a desired size. See, e.g., U.S. Pat. No. 4,737,323, and Hope et al., Biochim. Biophys. Acta, 812: 55-65 (1985), the relevant disclosures of each of which are incorporated by reference. Sonicating a liposome suspension either by bath or probe sonication produces a progressive size reduction down to small unilamellar vesicles less than about 50 nm in size. Homogenization or microfluidization are other methods which rely on shearing energy to fragment large liposomes into smaller ones. In a typical homogenization procedure, multilamellar vesicles are recirculated through a standard emulsion homogenizer until selected liposome sizes, typically between about 100 and 500 nm, are observed. In both methods, the particle size distribution can be monitored by conventional laser-beam particle size discrimination.

Extrusion of liposomes through a small-pore polycarbonate membrane or an asymmetric ceramic membrane is a very effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Any of the liposomes described herein can be analyzed by conventional methods to determine its physical and/or chemical features. For example, a phosphate assay can be used to determine liposome concentration. One phosphate assay is based on the interaction between molybdate and malachite green dye. The main principle involves the reaction of inorganic phosphate with molybdate to form a colorless unreduced phosphomolybdate complex which is converted to a blue colored complex when reduced under acidic conditions. Phosphomolybdate gives 20 or 30 times more color when completed with malachite green. The final product, reduced green soluble complex is measured by its absorbance at 620 nm and is a direct measure of inorganic phosphate in solution.

In other embodiments, the particles for drug delivery as described herein can be nanoparticles made of one or more polymers or co-polymers. For example, the nanoparticles can be poly(lactic-co-glycolic acid) (PLAG) nanoparticles, which can be prepared by routine technology.

(ii) Platelet-Membrane Proteins

The proteo-microparticles such as proteoliposomes (PLPs) described herein comprise one or more platelet membrane proteins, which preferably are displayed on the surface of the PLPs. In some embodiments, the one or more platelet membrane proteins present only on resting platelets and/or partially activated platelets, but not on activated platelet. The platelet membrane proteins may comprise p-selectin (CD62p), CD40L, CD18, or a combination thereof. Alternatively, the platelet membrane proteins are substantially free of CD40L, CD18, or both (e.g., include no CD40L, CD18, or both). In some embodiments, the platelet membrane proteins may comprise GPIIb, CD42c, and/or one or more proteins as listed in Table 2 blow, for example those that are involved in interaction with circulating blood cells, such as monocytes. In some examples, the PLPs described herein contains a mixture of membrane proteins isolated from resting and/or partially-activated platelets by conventional technology, such as the methods described in Examples below.

Platelet membrane proteins for use in preparing the PLPs described herein may be prepared by conventional methods or the methods described herein. For example, each of the proteins may be prepared via conventional recombinant technology and then incorporated into any of the liposomes described herein to form PLPs. Alternatively, the platelet membrane proteins may be purified from platelets, such as from resting or partially activated platelets following routine technology. The protein mixture may be incorporated into a suitable liposome. Alternatively, the protein mixture may be subject to further purification to enrich desired membrane proteins (e.g., by chromatography) and the enriched proteins can be used for preparing the PLPs.

In one example, the platelet-membrane proteins are isolated from resting or weakly (partially) activated platelets. PLPs prepared using membrane proteins isolated from resting or weakly activated platelets may have the advantage of not binding to endothelial cells so as to avoid thrombosis.

The one or more platelet membrane proteins can be inserted into liposomes as described herein to form proteoliposomes by any method known in the art. See, e.g., US 2005/0123594, the relevant disclosures of which are incorporated by reference herein for the intended purposes. In one example, a lipid solution comprising the components for preparing a liposome (e.g., lipids) as described herein can be mixed with platelet membrane proteins in the presence of a suitable detergent under conditions allowing for formation of proteoliposomes. The lipid-to-protein ratio may range from 30:1 to 50:1 (e.g., 30:1). The detergent and free proteins can be removed by extensive dialysis against a suitable buffer such as PBS at a suitable temperature (e.g., 4° C.). If needed, residual detergent can be removed by repeated BioBead treatments (SM-2; Bio-Rad).

(iii) Therapeutic Agents

Any of the proteoliposomes described herein may encapsulate a therapeutic agent, for example, a cardio-protective agent, e.g., an anti-inflammatory agent, an anti-apoptotic agent, an anti-fibrotic agent; an immuno-modulatory agent, or a proangiogenic agent.

Anti-inflammatory agents are compounds capable of suppressing inflammation. Examples include, but are not limited to non-steroidal anti-inflammatory drugs (NASIDs) such as aspirin, ibuprofen, and naproxen. Other examples include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofenin, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

Anti-apoptotic or cardio-protective agents are proteins, nucleic acids, or small molecule compounds that can inhibit apoptosis. Examples include IGFs, PDGFs, neuregulins, and angiopoietins.

Proangiogenic agents as used herein refer to chemical compounds (e.g., proteins, nucleic acid or small molecule compounds) that functions to stimulate the development of new blood vessels. The proangiogenic agent described herein can be a growth factor or cytokine that induces or promotes angiogenesis by stimulating endothelial cell growth or migration, for example, vascular endothelial growth factor (VEGF). Alternatively, the pro-angiogenic agent can be a member of the fibroblast growth factor (FGF) family such as FGF-1 (acidic), FGF-2 (basic), FGF-4 or FGF-5. Examples include trafermin, GENERX™, or an adenoviral gene therapy vector encoding FGF-4. Additional pro-angiogenic agents include angiopoietin-1. Specific examples of the proangiogenic agents for use in the present disclosure include, but are not limited to, VEGFs, FGFs, angiopoietins, and PDGFs.

Anti-fibrotic agents refer to chemical compounds (e.g., proteins, nucleic acids, or small molecule compounds) that have inhibitory activities against fibrosis, including abnormal formation of fibrous connective tissue, which is typically comprises of collagen. The anti-fibrotic agents described herein may have different mechanisms of action, e.g., reducing the formation of collagen or enhancing the metabolism or removal of collagen in the affected areas in the body. All such compounds having activity in the reduction of the presence of fibrous tissue are included herein, without regard to the particular mechanism of action by which each such drug functions. Examples include Nintedanib and Pirfenidone.

Immuno-modutory agents are proteins, nucleic acids, or small molecule compounds that can prevent or ameliorate undesired immune responses. Examples include Thalidomide, Lenalidomide, Pomalidomide, Apremilast and steroids.

Any of the therapeutic agents as described herein can be incorporated into a suitable proteoliposome as also described herein by a conventional method or a method described herein. In some embodiments, proteoliposomes can be loaded by imposing a pH gradient across the proteoliposome membrane (wherein the proteoliposome interior is acidic) and incubating the proteoliposome with the therapeutic agent to be encapsulated, as described, e.g., in Maurer et al., Expert Opinion in Biological Therapy 1, 923-47; NBoman et al., Cancer Res. 54, 2830-2833; Waterhouse et al., Methods Enzymol. 391 (2005) 40-57, hereby incorporated by reference for the intended purposes. In some examples, the pH gradient can be an ammonium sulfate gradient, as described generally in Haran et al., Biochim. Biophys. Acta 1115 (1993) 201-215 and U.S. Pat. No. 5,316,771, hereby incorporated by reference for the intended purposes. Once the therapeutic agent has been loaded into the proteoliposomes, the compositions can be used directly, or the composition can be further treated to remove any unloaded drug.

pH loading techniques generally involve two steps, the generation of the pH gradient with low intra-liposomal pH and the subsequent loading of the therapeutic agent. Transmembrane proton gradients can be generated by a variety of ways. For example, proteoliposomes can be prepared in a low pH buffer such as a pH 4 citrate buffer followed by exchange of the external buffer solution against a pH 7.5 buffer (e.g. Madden et al., Chem. Phys. Lipids, 53:37-46 (1990)). Alternatively, ionophores can be used in conjunction with cation gradients (high internal cation concentrations) (e.g., Fenske et al., Biochim Biophy. Acta, 1414:188-204 (1998)). Ionophores such as nigericin and A23187 couple the outward movement of monovalent or divalent cations, respectively, to the inward movement of protons thus acidifying the interior of the proteoliposomes. Furthermore, proteoliposomes can be prepared in the presence of high concentrations of a weak base such as ammonium sulfate (Haran et al., Biochim. Biophys. Acta, 1151:201-215 (1993)). Removal of the external ammonium salt solution results in the generation of a pH gradient according to the same principle, which is also responsible for the subsequent drug loading process.

In addition to pH gradients, metal ion gradients can also be used for active loading of a therapeutic agent. See, for example, Cheung et al., Biochim Biophys Acta, 1414:205-216 (1998), The neutral form of the weak base therapeutic agent can permeate across the membrane and is retained in the aqueous interior of the liposomes through formation of a drug-metal ion complex.

If the therapeutic agent is a water-soluble weak base drug, it may be dissolved in an aqueous solution (e.g., 300 mM sucrose, or isotonic buffer solutions with appropriate pH), combined with the proteoliposome suspension and then incubated at a suitable temperature. The drug solution can contain a small amount of a water-miscible organic solvent to increase the solubility of the drug (e.g., <10% ethanol). The incubation temperature and time depend on the lipid composition and the nature of the drug. Typically, liposomes composed of cholesterol and long-chain saturated fatty acids such as DSPC/cholesterol are less permeable than liposomes formed from short-chain saturated lipids (e.g., DMPC/cholesterol) or unsaturated lipids and require higher temperatures to achieve rapid and efficient loading. For example, DSPC/cholesterol liposomes typically require temperatures equal or higher than 60° C.; loading is typically complete after 5-15 minutes, but may take up to 2 hours.

If the therapeutic agent is lipophilic, the agent can be mixed with the lipids for making the proteoliposome under conditions that allow for distribution of the agent between the two monolayers of the liposome bilayer. The agent in the external monolayer can then be loaded into the liposome interior (flipped to the inner monolayer of the LN bilayer) in response to a trans-membrane pH or other ion gradient using the methods described herein.

Remote loading of compounds into proteoliposomes employs formation of transmembrane gradients as described in Ceh et al., Biochim Biophys Acta. 1995 Nov. 1; 1239(2): 145-56. This method includes incubating the therapeutic agent to be loaded into the proteoliposomes and a boronic acid compound with suspended proteoliposomes, thereby achieving accumulation of the therapeutic agent within the proteoliposomes (Ceh et al., 1995 and U.S. Pat. No. 6,051, 251).

Pharmaceutical Compositions and Uses Thereof

The present disclosure also provides pharmaceutical compositions comprising any of the proteo-microparticles such as proteoliposomes described herein, which may encapsulate one or more of the therapeutic agents also described herein, and a pharmaceutically acceptable carrier or excipient. The carrier in the pharmaceutical composition must be "acceptable" in the sense that it is compatible with the active ingredient of the composition, and preferably, capable of stabilizing the active ingredient and not deleterious to the subject to be treated.

Suitable carriers or excipients for the pharmaceutical compositions disclosed herein may be a substance that enhances the ability of the body of an individual to absorb the proteoliposome, facilitate binding of the proteoliposome to monocytes, and/or enhance endocytosis of the proteoliposome by macrophages developed from the monocytes. Suitable carrier and/or excipients also include any substance that can be used to bulk up formulations with a modified proteoliposome herein described, to allow for convenient and accurate dosage. In addition, carriers and/or excipients may be used in the manufacturing process to aid in the handling of a proteoliposome described herein. Depending on the route of administration, and form of medication, different carriers and/or excipients may be used. Exemplary excipients include but are not limited to antiadherents, binders, coatings disintegrants, fillers, flavors (such as sweeteners) and colors, glidants, lubricants, preservatives, sorbents. Carriers and/or expicients described herein may also include vehicles and/or diluents, wherein: "vehicles" indicates any of various media acting usually as solvents or carriers; "diluent" indicates a diluting agent which is issued to dilute an active ingredient of a composition; suitable diluent include any substance that can decrease the viscosity of a medicinal preparation.

The type and amounts of carriers and/or excipients are chosen in function of the chosen pharmaceutical form; suitable pharmaceutical forms are liquid systems like solutions, infusions, suspensions; semisolid systems like colloids, gels, pastes or cremes; solid systems like powders, granulates, tablets, capsules, pellets, microgranulates, minitablets, microcapsules, micropellets, suppositories; etc. Each of the above systems can be suitably be formulated for normal, delayed or accelerated release, using techniques well-known in the art.

Pharmaceutical compositions comprising the proteoliposomes described herein can be prepared according to standard techniques, as well as those techniques described herein. In some examples, the pharmaceutical compositions are formulated for parenteral administration, including intracanalicular administration, intravenous administration, subcutaneous administration, or intramuscular administration. In some examples, the pharmaceutical compositions are administered intravenously by a bolus injection or infusion. Suitable formulations for use in the present invention are found in Remington's Pharmaceutical Sciences, Mack Publishing Company, Philadelphia, Pa., 17th ed. (1985).

In some examples, the pharmaceutical composition is formulated for injection, such as intravenous infusion. A sterile injectable composition, e.g., a sterile injectable aqueous or oleaginous suspension, can be formulated according to techniques known in the art using suitable dispersing or wetting agents (such as Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically.

Any of the pharmaceutical compositions can be used for delivering a therapeutic agent to a desired target site using circulating monocytes as carriers. To practice this use, an effective amount of a pharmaceutical composition comprising any of the proteoliposomes described herein, which encapsulates a therapeutic agent (e.g., an anti-inflammatory agent), can be administered to a subject in need of the treatment (e.g., a human subject) via a suitable route, such as those described herein. Via the binding activity to monocytes, the proteoliposomes would be associated with circulating monocytes of the subject and be delivered to a site where monocytes accumulate (e.g., a site where inflammation occurs). Once the monocytes cross the endothelial cell layers, they differentiate into macrophages, which absorb the associated proteoliposomes via endocytosis, thereby releasing the entrapped therapeutic agent to exert its therapeutic effects.

"An effective amount" as used herein refers to the amount of each active agent required to confer therapeutic effects on the subject, either alone or in combination with one or more other active agents. Effective amounts vary, as recognized by those skilled in the art, depending on route of administration, excipient usage, and co-usage with other active agents.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the pharmaceutical composition, comprising an anti-inflammatory agent as described herein, is for use in treating an ischemic heart-disease (IHD). The term "treating" as used herein refers to the application or administration of a composition including one or more active agents to a subject, who has an allergic disease, a symptom of the allergic disease, or a predisposition toward the allergic disease, with the purpose to cure, heal, alleviate, relieve, alter, remedy, ameliorate, improve, or affect the disease, the symptoms of the disease, or the predisposition toward the disease.

After being administered into a subject having, suspected of having, or at risk for an IHD, e.g., a human IHD patient, the proteoliposome can be delivered to an infarct heart area via attaching to monocytes and to exert the desired therapeutic effects at the target site. IHD is a disease characterized by reduced blood supply to the heart due to, e.g., atherosclerosis. Symptoms associated with IHD include, but are not limited to, chest pain or discomfort.

Kits

The present disclosure also provides kits for use in delivering therapeutic agents to a target site or for use in treating an IHD by delivering an anti-IHD agent, such as an anti-inflammatory agent, to an infarct heart area. Such kits can include one or more containers comprising any of the pharmaceutical compositions described herein, which comprises a proteo-microparticle such as a proteoliposome or a nanoparticle alike encapsulating the therapeutic agent and a pharmaceutically acceptable carrier.

In some embodiments, the kit can comprise instructions for use in accordance with any of the methods described herein. The included instructions can comprise a description of administration of the pharmaceutical composition for delivering the therapeutic agent encapsulated therein or for treating an IHD according to any of the methods described herein. The kit may further comprise a description of selecting an individual suitable for treatment based on identifying whether that individual has, is suspected of having, or is at risk for IHD. The instructions relating to the use of the pharmaceutical composition described herein, which comprises a proteoliposome encapsulating a therapeutic agent, generally include information as to dosage, dosing schedule, and route of administration for the intended treatment. The containers may be unit doses, bulk packages (e.g., multidose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for delivering the therapeutic agent to a target site or for treating an IHD. Instructions may be provided for practicing any of the methods described herein.

The kits as described herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer), or an infusion device such as a minipump. A kit may have a sterile access port (for example the container may be an intravenous solution bag or a vial having a stopper pierceable by a hypodermic injection needle). The container may also have a sterile access port (for example, the container may be an intravenous solution bag or a vial having a stopper pierceable by a hypodermic injection needle).

The kits described herein may optionally provide additional components such as buffers and interpretive information. Normally, the kit comprises a container and a label or package insert(s) on or associated with the container. In some embodiments, the present disclosure provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Examples: Biomimicking Platelet-Monocyte Interactions as a Novel Strategy of Targeted Therapy of Acute Myocardial Infarction Development of effective cardio-protective treatment strategies continues to be a challenge as many potential cardio-protective drugs fail to translate from the bench into clinical results. One of the key issues is the optimization of targeted drug delivery to the infarcted heart. Although several drug delivery systems have been reported to actively deliver encapsulated drugs to the infarct area, the functionalized surfaces on these delivery systems only allow them to be better retained at targeted sites or have a higher circulation half-life. Thus, an enhanced permeability and retention (EPR) effect is still required as a main route of drug delivery for these delivery systems.

Figure 1B:
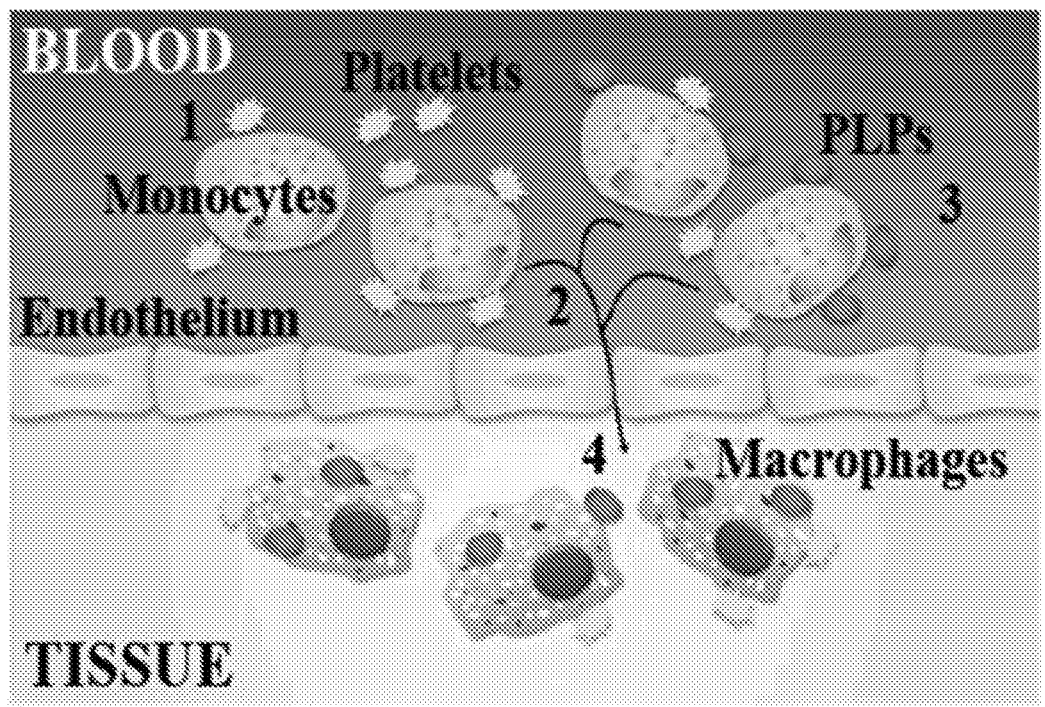

The present study provides a novel drug delivery system that allows for delivery of cardio-protective drugs to heart infarct areas without relying on the EPR effect. This new drug delivery system mimics the platelet interaction with the circulating monocytes during post-myocardial infarction (MI). For example, platelet-like proteoliposomes (PLPs) were fabricated using purified human platelet membrane proteins and lipids such as 1,2-dioleoyl-sn-glycero-3-phosphocholine (DOPC) lipids. This strategy is outlined in FIG. 1B. In vitro data showed that PLPs displayed a strong affinity for monocytes and macrophages but not for endothelial cells. Intravital multiphoton imaging revealed that the PLPs had better targeting to the tissue injury site than the plain liposome control. When injected at 72 hours of reperfusion, which is when the monocyte recruitment reaches the maximum level, there were significantly more PLPs at the infarcted heart areas than in the controls areas. Moreover, cobalt protoporphyrin (CoPP) encapsulated in PLPs (PLP-CoPP) was shown to improve the cardiac function in a murine model of MI while reducing the adverse effect of the encapsulated drug.

Results obtained from the present study show that the PLP system described herein can be used effectively to deliver drugs to a desired site such as infarcted heart areas.

Materials and Methods

Animal Experimentation

Eight-week-old male BALB/c mice, used for all investigations, were purchased from the National Laboratory Animal Center, Taiwan and were kept in a 12-hour night/day cycle with free access to food and water.

Surgery for myocardial ischemia-reperfusion (I/R) was performed according to the protocol published in Ojha et al. ((2008), Am J Physiol Heart Circ Physiol 294:H2435-H2443). Briefly, the mice were ventilated on room air-isoflurane at an appropriate rate and tidal volume. The heart was accessed via left thoracotomy, in which the left lung was retracted to allow entrance to the pericardium. Subsequently, the left atrium was elevated to expose the left anterior descending coronary artery (LAD), and was isolated using a 7-0 silk suture on a taper needle. The suture was tightened over a piece of polyethylene-10 tubing to provide for reversible ischemia via the occlusion of the coronary artery. Ischemia was allowed to continue for 45 minutes after occlusion. After 45 minutes, the suture was released to allow for reperfusion of the injured myocardium. The following day, echocardiography was performed on the mice to access the success of the surgery. Similarly, a murine model of myocardial ischemia (MI) was surgically performed by permanently ligating the LAD at 2-3 mm distal to the left atrial appendage.

Echocardiography

The cardiac function in murine models of both I/R and MI was assessed by using a 30-MHz probe (Vevo770; Visual Sonics, Toronto, ON, Canada), following the methods published in Chen et al. ((2015), Stem Cells Trans Med 4:269-275). Mice were first placed in the left lateral decubitus position. Parasternal long axis views were obtained with both M-mode and 2-dimensional echocardiographic images. The left ventricular end-diastolic diameter (LVEDD) and end-systolic diameter (LVESD) were measured perpendicular to the long axis of the ventricle at the location of the papillary muscle insertion site. The LVEF was calculated automatically by the echocardiography system as (LVEDV-LVESV)/LVEDV×100%, where LVEDV is the left ventricular end-diastolic volume, calculated as $7.0 \times LVEDD^3/(2.4+LVEDD)$, and LVESV is the left ventricle end-systolic volume, calculated as $7.0 \times LVESD^3/(2.4+LVESD)$.

Isolation of Human Platelets and Purification of Platelet Membrane Proteins

Unactivated or partially activated platelets were harvested from human donors under ethics approval from the Institute of Biomedical Science, Academia Sinica. Blood was collected in acid citrate dextrose (ACD) anticoagulant treated vacutainers (BD Sciences, Cat #366450). Platelet rich plasma (PRP) was prepared by centrifugation of the blood at 350×g for 20 minutes at room temperature. The upper layer (PRP) was moved into a new tube, and the bottom layer was discarded. PRP was then centrifuged at 1,200×g for 10 minutes at room temperature to yield a platelet pellet with platelet poor plasma as the supernatant. The platelet pellet was resuspended in Tyrode's buffer (1.8 mM $CaCl_2$, 1 mM $MgCl_2$, 2.7 mM KCl, 136.9 mM NaCl, 0.4 mM $NaH2PO4$, 11.9 mM $NaHCO_3$, 5.6 mM D-glucose and 0.1 U/mL apyrase) and centrifuged again at 1,200×g for 10 minutes at room temperature. The supernatant was discarded, and the platelets were resuspended in 1 mL Tyrode's buffer.

Figure 1C:
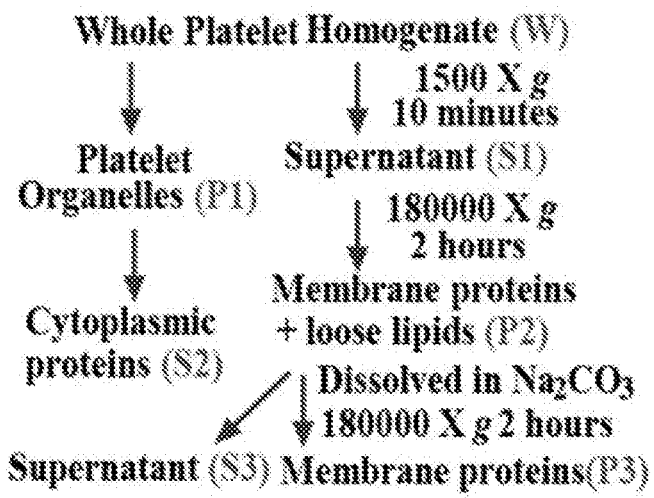

The method for purifying human platelet membrane proteins (PMPs) was based on the protocol published in Donovan et al. ((2013), Alzheimer's Res Ther 5:32), with some modifications. Briefly, the purified human platelet pellet was resuspended in Tyrode's buffer and centrifuged at 1,100×g for 15 minutes at room temperature, and then the pellet was resuspended in 5 mL platelet lysis buffer (10 mM Tris HCl, 1.5 mM $MgCl_2$, 10 mM KCl, 0.5 mM PMSF, pH 8) and incubated on ice for 30 minutes. Subsequently, the resuspended platelet solution was sonicated for 6×15 seconds while on ice, and then centrifuged at 1,500×g, for 10 minutes at room temperature, in which the separated platelet organelles were discarded, and the rest of the platelet protein component, in supernatant, was kept. After centrifugation at 4° C., 180,000×g for 2 hours, the pellet was resuspended in 100 mM $Na_2CO_3$, pH 11 on ice for 15 minutes to strip the remaining lipid residues from the protein component. The solution was then centrifuged at 4° C., 180,000×g for 2 hours, and the pellet was resuspended in sterilized water. FIG. 1C illustrates an exemplary process of purifying PMPs from whole platelet homogenate.

Protein Identification

Identification of membrane proteins in the purified human platelet membrane protein solution was performed by IBMS Protein Core Facility (Academia Sinica, Taiwan).

Cells

Murine endothelial cells, SVECs (CRL-2181, ATCC), and monocytes, RAW264.7 cells (TIB-71, ATCC), were cultured in in Dulbecco's modified Eagle's medium (DMEM) containing 2 mM glutamine and 10% fetal calf serum. Murine peritoneal macrophages (MΦ) were isolated from adult mice according to Zhang et. al. ((2008), Curr Protoc Immunol 14:14.1). Briefly, the mice were exposed to 2 mL 3% thioglycollate for at least 3 days. Cold PBS (10 mL) was used to harvest the peritoneal exudate cells. The cells were allowed to adhere to tissue culture plates for 2 hours at 37° C., followed by the exchange of fresh media (DMEM/F-12+10% FBS).

SDS-PAGE and Western Blotting

Samples were separated on 4-12% SDS-polyacrylamide gels (BioRad, US). After transfer to PVDF membrane, primary and secondary antibodies were applied, and the signals were detected with ECL-plus reagent. Primary antibodies against human GPIIb (GTX113758), human CD42c (GTX113355) and β-actin (GTX109639) were purchased from GeneTex (US). The anti-human CD62P (sc-19672) were from Santa Cruz (US). The rabbit polyclonal anti-HO-1 antibodies were made in-house according to Lin et al. ((2013), Arterioscler Thromb Vasc Biol 33:785-794).

Histological Staining

Samples were dehydrated for 6 hours in sucrose solution (1.5% w/v) and then overnight in concentrated (30% w/v) sucrose solution before being embedded in tissue freezing medium at −20° C. and cryosectioned. Each section, 5 μm thick, was mounted on a glass slide and then stained with hematoxylin-eosin following the standard Masson's trichrome staining protocol. The stained sections were photographed using a digital camera (model D30; Hitachi, Japan) mounted on a microscope (Axiovert200M; Zeiss, Germany).

Immunofluorescence Imaging

Plain liposomes and PLPs were labeled with DiIC18 (Life Technologies, US). Subsequently, both DiI-labeled materials were examined for their interactions with different cell types. The cells were first seeded onto glass slides and exposed to either material for 6 hours at 37° C. Any unbound materials were washed away with warm PBS. Afterward, the cells seeded on the glass slides were covered with cover slips and images were captured on a Zeiss Axioscope microscope and processed with Axio Vision software. The immunodetection of DiI-labeled plain liposomes and PLPs in the frozen sectioned heart was labeled with anti-murine troponin 1 (DSHB, US) to stain for murine cardiomyocytes and nuclei were counterstained With DAPI (0.1 mg/mL). Images were also taken with a Zeiss Axioscope microscope and processed with AxioVision software.

Non-Myocyte Cell Isolation

After a heart was excised from an adult mouse, the tissue was washed three times with cold Hank's Balanced Salt Solution (HBSS)+1% FBS. The heart was perfused to remove excess blood, and then placed in 200 μL of Dispase II solution (5 U/mL Dispase II, 5 mM $CaCl_2$, 0.1 U/mL collagenase B). The heart was then diced into a fine mesh using a razor blade, followed by incubation in 5 mL of Dispase II solution at 37° C. for 30 minutes. Subsequently, 5 mL of DMEM+10% FBS was added to the solution and filtered through a 40 μm filter on ice. The filtrate was kept and centrifuged at 1,000 rpm for 5 minutes at 4° C. The pellet was then subjected to flow cytometry analysis.

Flow Cytometry

After the cells had been exposed to either DiI-labeled plain liposomes or DiI-labeled PLPs, the cells were rinsed off with warm PBS. The unbound plain liposomes or PLPs were removed by centrifugation at 1,000 rpm for 5 minutes at room temperature. Subsequently, the cell pellets were incubated with a mixture of 5% goat serum for 30 minutes on ice. After being centrifuged at 1,000 rpm for 5 minutes at 4° C., the samples were incubated with their respective primary antibodies: anti-murine F4/80 APC conjugated (MCA497APC, AbDSerotec, US), anti-murine CD11b (14-0112, eBioscience, US), or anti-CD144 (555289, BD Science, US) for 1 hour in the dark at 4° C. Excess primary antibodies were removed by centrifugation at 1,000 rpm for 5 minutes at 4° C. Subsequently, the samples were incubated with their respective fluorescent-labeled secondary antibodies for 1 hour in the dark at 4° C. After the excess secondary antibodies were removed by centrifugation, the samples were subjected to flow cytometry analysis (BD Science, US).

PCR Analysis

Total RNA was isolated from a whole heart using TRI Reagent (1 mL/whole heart). Subsequently, 1 μg of RNA was transcribed info cDNA using a random primer mixer (ProtoScript M-MuLV First Strand cDNA synthesis kit, New England BioLabs) and amplified during 35 cycles by PCR, utilizing specific primers (Table 1). The reactants were cycled at 95° C. for 1 min, 58° C. for 1 min, and 72° C. for 1.5 min to enable denaturation, annealing, and extension, respectively. PCR products were then separated on 1% (w/v) agarose gel at 60 V for 1 hour in TBE buffer (80 mM Tris base, 80 mM boric acid, and 2 mM EDTA, pH 8). The gels were stained with Health View Nucleic Acid Stain (Genomics, Taipei, Taiwan) for 30 minutes and then visualized under UV light.

TABLE 1

Primer Sequences

| Genes | Sequences | SEQ ID NO: |
|---|---|---|
| HO-1 | F-GAGCAGAACCAGCCTGAACT | 1 |
|  | R-TTTGAACTTGGTGGGGCTGT | 2 |
| TNF-α | F-TAGCCCACGTCGTAGCAAAC | 3 |
|  | R-ACCCTGAGCCATAATCCCCT | 4 |
| MCP-1 | F-GATGCAGTTAACGCCCCACT | 5 |
|  | R-ACCCATTCCTTCTTGGGGTC | 6 |
| IL-1β | F-TGCCACCTTTTGACAGTGATG | 7 |
|  | R-TTCTTGTGACCCTGAGCGAC | 8 |
| IL-6 | F-GCCTTCTTGGGACTGATGCT | 9 |
|  | R-TGGAAATTGGGGTAGGAAGGAC | 10 |

Preparation of Platelet-Like Proteoliposomes

The preparation of platelet-like proteoliposomes was based on the thin-film hydration method. Jang et al., (2012), PNAS 109:1679-1684. An exemplary process is outlined in FIG. 1A. Stock solutions of 10 mg/mL each of 1,2-dioleoyl-sn-glycero-3-phosphocholine (DOPC) and 3.28 mg cholesterol (Avanti Polar Lipids) were dissolved in 1 mL of chloroform and methanol (9:1 v/v) and mixed in a molar ratio of 6:4 by volume, respectively. A thin film was formed by rotary evaporator. If the lipids were to be pre-labeled with DiIC18 (Life Technologies, US), then the dye was added to the original mix before the thin-film formation step (20 μL per 10 mg of DOPC). The film was then resuspended in 1 mL HEPES-PBS buffer, and the final lipid concentration was approximately 10 mg/mL. After several rounds of freeze-thawing, the lipid solution was extruded through a 100 nm polycarbonate membrane (Whatman, US).

The formulated lipid solution was then mixed with purified human platelet membrane proteins in the presence of 1% n-octyl-β-D-glucopyranoside (OG) at a ratio of 30:1 for one hour at room temperature. The detergent was removed by using the SM2-BioBeads according the manufacturer's protocol (BioRad). Afterwards, the PLPs were separated from the beads by centrifugation at 6,000×g for 5 minutes at 4° C. The supernatant, which contained the detergent-free proteoliposomes was dialyzed against PBS overnight at 4° C. to remove any unbound human PMPs. The encapsulation of cobalt protoporphyrin (CoPP, Enzo) with PLPs was performed according to Hamori et al. ((1993), Pediatr Res 34:1-5). The desired amount of CoPP to be encapsulated was mixed with the detergent-free PLPs solution, and then frozen in liquid nitrogen. Subsequently, the mixture was lyophilized overnight. The following day, the lyophilized product was hydrated with PBS and centrifuged at 80,000 rpm for 2 hours at 4° C. The pellet was resuspended and ultracentrifugation was repeated for another hour to wash away excess CoPP. Finally, the pellet was resuspended in the desired volume of PBS.

HPLC Quantification

Sample preparations for subsequent HPLC analysis were performed according to Chen et al. ((2015), Nanoscale 7:15863-15872). Four hours after the injection of either DiI-labeled plain liposomes or PLPs, all mice were perfused with PBS to wash away all the DiI-labeled materials in the vessels. Afterwards, the animals were sacrificed and the major organs (brain, lungs, heart, liver, kidneys and spleen) were rapidly harvested. The harvested tissues were cut into several ~100 mg pieces and weighed. IPA buffer (0.5 mL, 10% isopropanol mixed with 0.075 M HCl, 9:1 v/v) was added to each sample, followed by thorough homogenization using a MagNALyser instrument With zirconia beads (Roche, Mannheim, Germany). Homogenized samples were then centrifuged at 3,000 rpm for 20 seconds at 4° C., followed by another addition of 0.5 mL of IPA buffer. After leaving the samples at 4° C. overnight, the samples were centrifuged at 14,000 rpm for 15 minutes at 4° C. The supernatant, containing the extracted fluorescent dye, was withdrawn, diluted, and subjected to HPLC analysis. HPLC was carried out using a Waters e2695 Separation Module and Waters 2475 FLR Detector (USA). An X-Bridge C18 column (250×4.6 mm, 5 μm, Waters, USA) was used at 40° C. and the fluorescence detector was set to an excitation wavelength of 505 nm and emission wavelength of 515 nm. The mobile phase consisted of methanol and de-ionized water (77:23, v/v) with a flow rate of 1 mL/min. HPLC standards were measured by serial dilutions of known concentration of either DiI-labeled plain liposomes or PLPs.

The encapsulation efficiency of CoPP in either plain liposomes or PLPs was determined by measuring the amount of CoPP liberated from plain liposomes or PLPs after treating both plain liposome-encapsulated CoPP (Lipo–CoPP) and PLP-encapsulated CoPP (PLP–CoPP) solutions with the lysing buffer (90% ethanol/10% 1M HCl, v/v). The solutions were subjected to HPLC analysis. An X-Bridge C18 column (250×4.6 mm, 5 μm, Waters, USA) was used at 40° C. and the UV detector was set to an excitation wavelength of 404 nm and emission wavelength of 417 nm. Rossi et al., (1986), Biomed Chrom 1:163-168. A standard curve of a known concentration of CoPP was constructed and the encapsulation efficiency for each sample was determined.

Cryo-EM and TEM

The sample preparation and photography for the cryo-EM images were performed by independent staff at the Cryo-EM Core Facility, Department of Academic Affairs and Instrument Service at Academia Sinica, Taiwan. Briefly, images of the plain liposomes or PLPs were obtained by using a Tecnai F20 electron microscope (FEI) at 200 keV. The low dose condition for each exposure was approximately 20 e-/Å2. Images were taken at 2 to 3 μm defocus and recorded on a 4 k×4 k CCD camera (Gatan, USA).

The TEM images showing macrophages with the phagocytized PLPs were photographed by the independent staff at the Transmission Electron Microscope Core Facility, Institute of Biomedical Sciences, Academia Sinica, Taiwan. The sample was prepared by first seeding the cells onto an ACLAR film (EMS, US) overnight at 37° C. Subsequently, the seeded cells were exposed to PLPs for 6 hours at 37° C., and excess PLPs were washed away by warm PBS. The samples were then subjected to TEM imaging.

Intravital Multiphoton Microscopy

Imaging procedures for the intravital multiphoton imaging experiment was conducted as previously described in Lee et al. (2012), Nat Commun 3:1054). Before the experiment, the ears were depilated and wiped with 75% ethanol and water. Laser injury was induced by focusing the multiphoton laser beam at a confined region within the ear dermis for approximately 30 seconds. All animals were anesthetized with 2.5% isoflurane (Minrad), and then maintained on 1.5% isoflurane during the experiment. FITC-dextran was intravenously injected via the tail vein to label the blood vessels of the mice that were designated into either a plain liposome or PLP treatment group (n=3). After 4 hours of stabilization, the tissue injury area was imaged using a FVMPE-RS multi-mode multiphoton scanning microscope (Olympus). Subsequently, 100 μL of 5 mg/mL of either DiI-labeled plain liposomes or PLPs was intravenously injected via the tail vein and the tissue injury area in the ear was observed immediately afterwards for up to 30 minutes, at which point images were taken every 5 minutes.

HO-1 Activity Assay

To determine the specific activity of the induced HO-1, expression in CoPP exposed cells, the amount of bilirubin in the analyzed cell extract was measured. Lam et al. (2005), J Immunol 174:2297-2304. Cell pellets were resuspended in magnesium-supplemented potassium phosphate solution (0.1 M $KPO_4$ and 2 mM $MgCl_2$; pH 7.4) and subjected to three freeze-thaw cycles and sonication for the release of cytoplasmic HO-1 proteins. The HO-1 enzymatic assay used a reaction mixture containing 100 mM PBS, 2 mM $MgCl_2$, 3 mg rat liver cytosol, 0.8 mM NADPH, 2 mM glucose-6-phosphate, 0.2 U glucoses-6-phosphate dehydrogenase, and 20 μM enzyme substrate hemin and 1 mg of sample. The reaction was made up to a final volume of 1 mL for each sample and was incubated at 37° C. for 1 hour in the dark. Chloroform was added to terminate the reaction, and bilirubin was extracted following centrifugation and measured by spectrophotometry as the difference in absorbance between 464 and 530 nm (extinction coefficient for bilirubin 40 $mM^{-1}$ $cm^{-1}$). The protein concentration in each sample was determined with a Bradford protein assay, and the HO-1 activities were expressed in micromoles of bilirubin formed per milligram of protein per hour.

Blood Tests

All blood tests were performed by independent staff at the Taiwan Mouse Clinic, Academia Sinica, Taiwan. Male, BALB/c mice, approximately 56 weeks old, were used for all analyses (n=5 per group).

Statistical Analysis

One-way ANOVA (analysis of variance) test, and then Tukey post-hoc test were used to compare the statistical significance between treatments under test conditions. A p value of less than 0.05 was considered significant.

Results

Purification of Platelet Membrane Proteins from Human Platelets

Figure 1D:
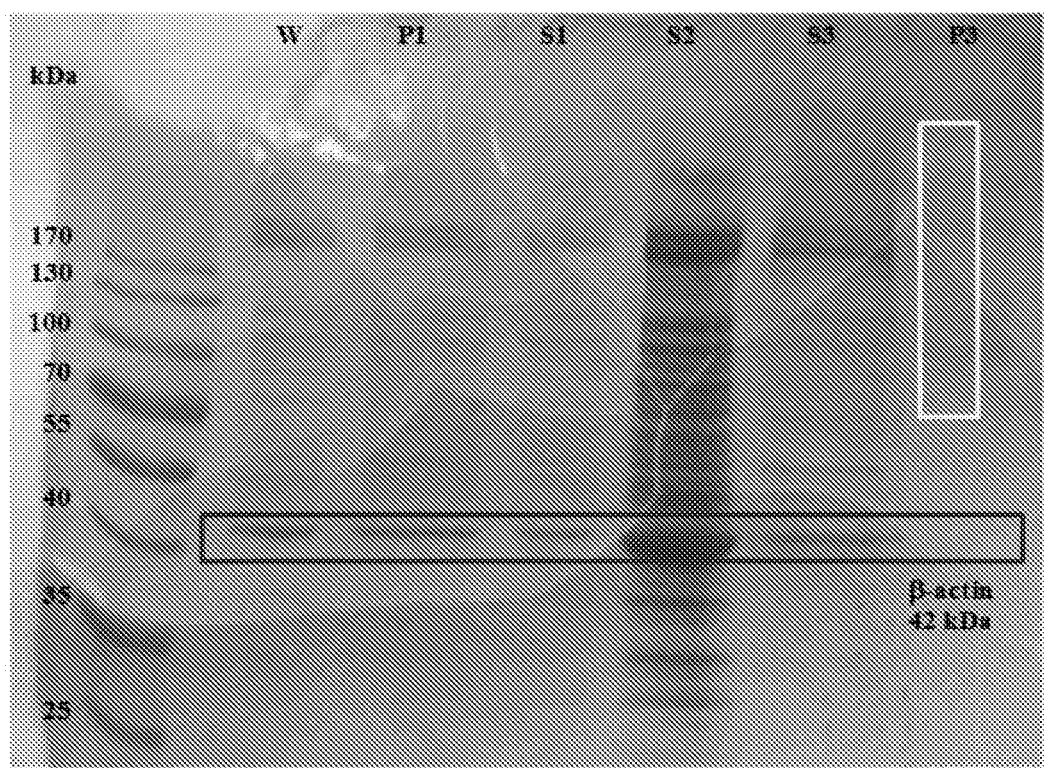
Figure 1E:
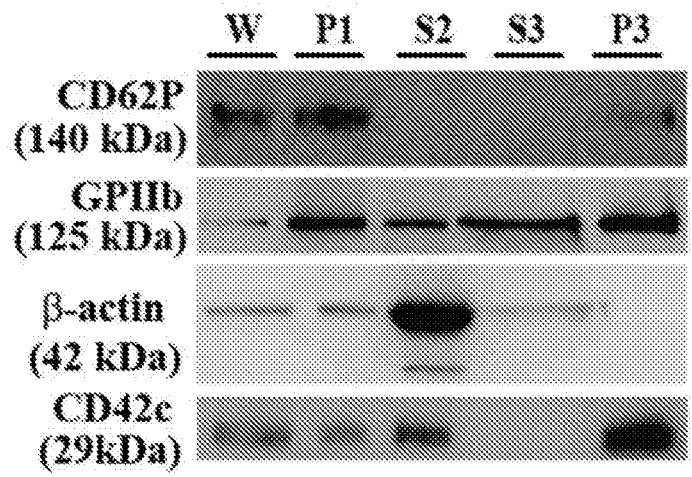

To ensure the purified platelet membrane protein solution did not contain any cytoplasmic proteins, SDS-PAGE and Western blotting analysis were performed (FIGS. 1D and 1E, respectively). The SDS-PAGE revealed multiple bands in the lane loaded with purified PMPs, which likely represent different PMPs (white box, FIG. 1D). A common band at the position of ~42 kDa, representing β-actin (Moebius et al., (2005), Mol Cell Proteomics 4:1754-1761), was detected in all samples except in the purified human PMPs (black box, FIG. 1D). Since β-actin is a major cytoplasmic protein in platelets (Lewandrowski et al., (2009), Blood 114-E10-E19), its absence suggested that the purified PMP solution is substantially free of cytoplasmic protein contamination. The identity of some of the detected bands was then confirmed by Western blotting.

As shown in FIG. 1E, platelet proteins such as CD62, GPIIb, and CD42c, were detected in the PLP samples, while β-actin was not detected. CD62P (P-selectin) is an activated platelet receptor well-known for its interaction with the p-selectin glycoprotein ligand-1 (PSGL-1) on monocytes, whereas fibrinogen bridges the interaction of GPIIb (integrin $\alpha_{IIb}$) with the CD11b (integrin $\alpha_M$) on monocytes. Platelet CD42c (GPIb) has been shown to directly interact with CD11b on monocytes. Along with other known platelet receptors that interact with monocytes, the identities of the three platelet receptors in the purified PMP solution was also confirmed by mass spectrometry analysis (Table 2). Both GPIIb and CD42c are constitutively expressed on the surfaces of platelet membranes, whereas CD62P is an early platelet activation marker, which may be "weakly" induced via needle puncturing. Murakami et al., (1996), European J of Clin Invest 26:966-1003; Marquardt et al., (2002), Stroke 33:2570-2574; Harmon et al., (2011) Int Cellular Med Society 1-11.

TABLE 2

Platelet membrane proteins identify by protein mass spectrometry

| Name | Mass (Da) |
|---|---|
| Integrin alpha-IIb | 113,306 |
| Integrin beta-3 | 87,000 |
| Platelet glycoprotein 4 (CD36) | 53,019 |
| Band 3 anion transport protein | 101,727 |
| Platelet glycoprotein V | 60,921 |
| Integrin alpha-6 | 126,526 |
| HLA class I histocompatibility antigen, A-24 alpha chain | 40,663 |
| HLA class I histocompatibility antigen, B-58 alpha chain | 40,312 |
| HLA class I histocompatibility antigen, B-35 alpha chain | 40,430 |
| HLA class I histocompatibility antigen, Cw-12 alpha chain | 40,860 |
| Platelet glycoprotein Ib alpha chain | 71,495 |
| HLA class I histocompatibility antigen, B-57 alpha chain | 40,199 |
| Platelet endothelial cell adhesion molecule | 82,484 |
| HLA class I histocompatibility antigen, A-23 alpha chain | 40,707 |
| HLA class I histocompatibility antigen, A-3 alpha chain | 40,815 |
| HLA class I histocompatibility antigen, A-34 alpha chain | 41,029 |
| HLA class I histocompatibility antigen, A-33 alpha chain | 40,866 |
| Integrin alpha-2 | 129,214 |
| Integrin beta-1 | 88,357 |
| CD9 antigen | 25,399 |
| P-selectin | 140,073 |
| Platelet glycoprotein IX | 19,034 |
| Junctional adhesion molecule C | 35,020 |
| Intercellular adhesion molecule 2 | 30,635 |
| Platelet glycoprotein Ib beta chain | 21,704 |
| Solute carrier family 2, facilitated glucose transporter member 1 | 54,049 |
| CD226 antigen | 38,589 |
| Transmembrane protein 40 | 25,479 |
| Multiple C2 and transmembrane domain-containing protein 2 | 99,533 |
| Leukocyte surface antigen CD47 | 35,191 |
| Transmembrane protein 33 | 27,960 |
| Platelet glycoprotein VI | 36,843 |
| CD151 antigen | 28,276 |

One or more platelet membrane proteins listed in the above table can be used for making the PLPs described herein. In some examples, at least one of the proteins in boldface, which are identified as being involved in platelet-monocyte interaction, is used for making the PLPs described herein.

PLPs are Fabricated by Reconstituting Human PMPs with DOPC-Based Liposomes

Figure 1F:
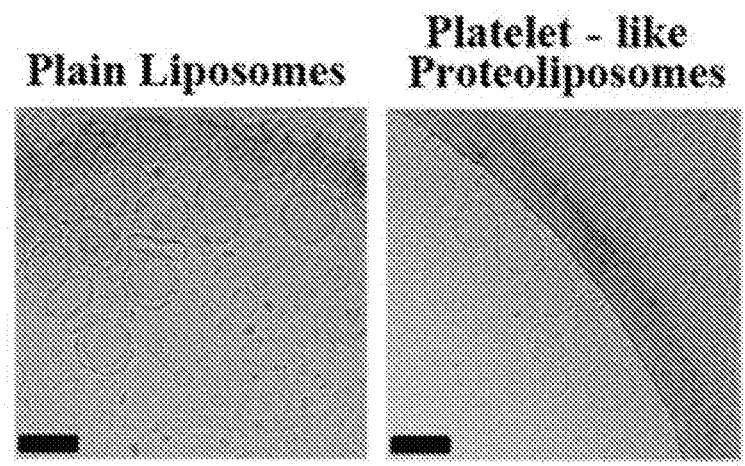
Figure 1G:
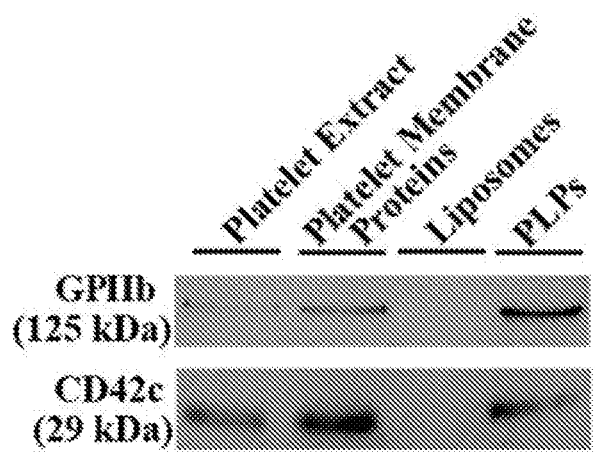

Batches of PLPs were prepared by the thin film hydration method (Jang et al., (2012), PNAS 109:1679-1684), which consists of a mixture of DOPC and cholesterol (9:1, w/w), and the purified human PMPs in a ratio of 30:1. In the cryo-EM image, the plain liposomes displayed irregular shapes and aggregation (FIG. 1F). In comparison, uniformly circular shapes were seen for PLPs. However, the cryo-EM image showed there was inconsistency in the size of PLPs, as not all PLPs were around 100 nm in size. Dynamic light scattering (DLS) measurement revealed a similar result in that, on average, most PLPs had a size close to 100 nm (PDI=0.077), whereas the plain liposomes had an average size of approximately 130 nm (PDI=0.12, Table 3). Importantly, the overall surface charge of PLPs was shown to be more negative compared to plain liposomes. This suggested that the conjugation of human PMPs to DOPC-based liposomes was successful, as platelet membrane proteins are known to be negatively charged. Lewandrowski et al., (2009), Blood 214:E10-E19. Moreover, the presence of human PMPs on PLPs was confirmed by Western blotting (FIG. 1G), as both anti-human GPIIb and CD42c antibodies had positive reactivity with the PLPs but not with the plain liposomes.

TABLE 3

Physical characterization of DOPC-based liposomes and PLPs

| | Z-average (nm) | Zeta Potential (mV) | PDI |
|---|---|---|---|
| Liposomes | 128.33 ± 4.77 | −0.47 ± 0.21 | 0.12 ± 0.012 |
| PLPs | 100.47 ± 5.97** | −2.25 ± 0.05*** | 0.077 ± 0.004 |

Size, surface charges, and polydispersity index (PDI) of three different batches of DOPC-based liposomes and PLPs (n=3) were measured by Malvern Zetasizer Nano ZS. The hydraulic diameter and the zeta potential of PLPs were statistically compared with liposomes. , $P<0.01$, *, $P<0.001$.

PLPs Show Targeting Specificity for Monocytes But Not for Endothelial Cells

Figure 3A:
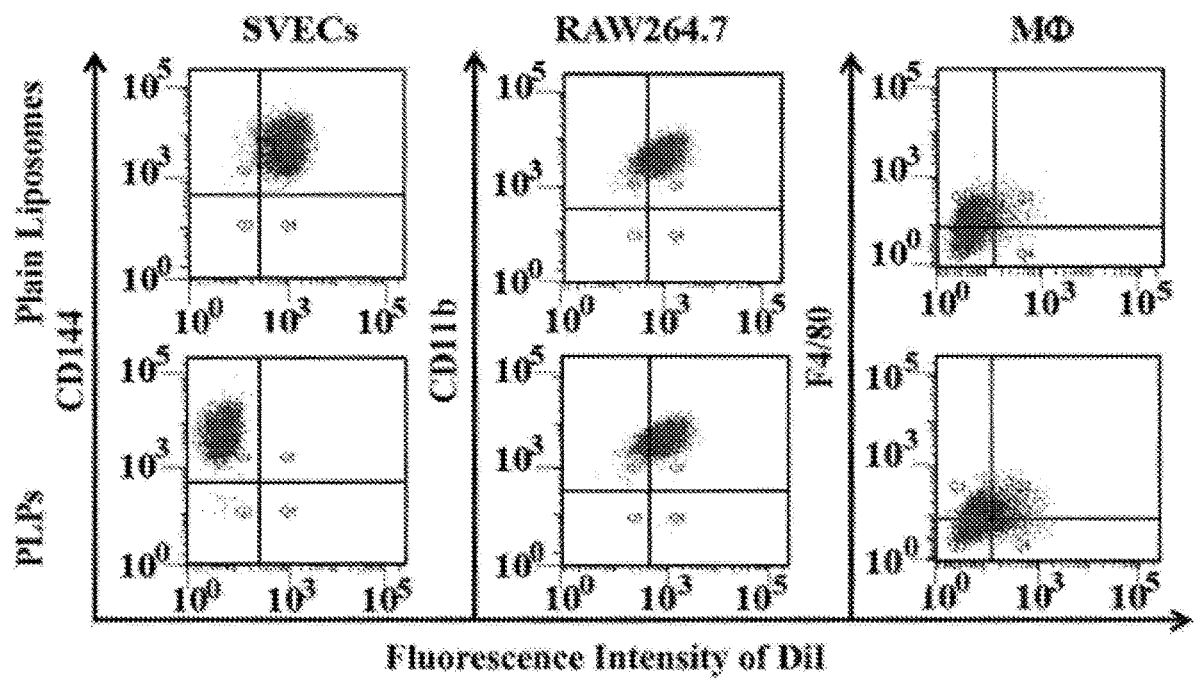
FIGS. 3A-3E show the targeting specificity of PLPs. Murine endothelial cells (SVECs), monocytes (RAW264.7), and murine peritoneal macrophages (MΦ) were exposed to either DiI-labeled liposomes or DiI-labeled PLPs at 37° C. for 4 hours, before being subjected to flow cytometry analysis (FIG. 3A). The exposure of PLPs to MΦ resulted in vacuole formation (white arrows); scale bar, 2 μm (FIG. 3B). The presence of PLPs in MΦ was also visible by TEM (white arrows); scale bar, 0.2 μm (FIG. 3C). The interactions of either DiI-labeled liposomes (FIG. 3D) or DiI-labeled PLPs (FIG. 3E) with the three cell types were visualized by fluorescence imaging; scale bar, 10 μm.
Figure 3B:
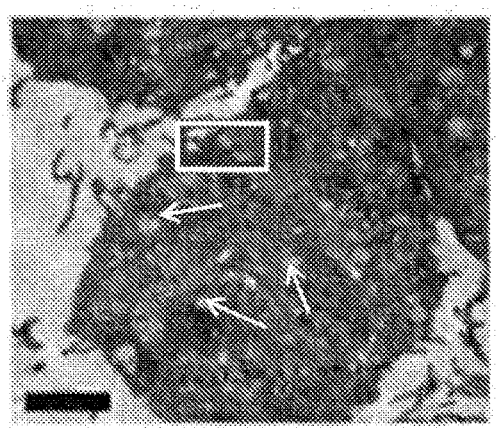
Figure 3C:
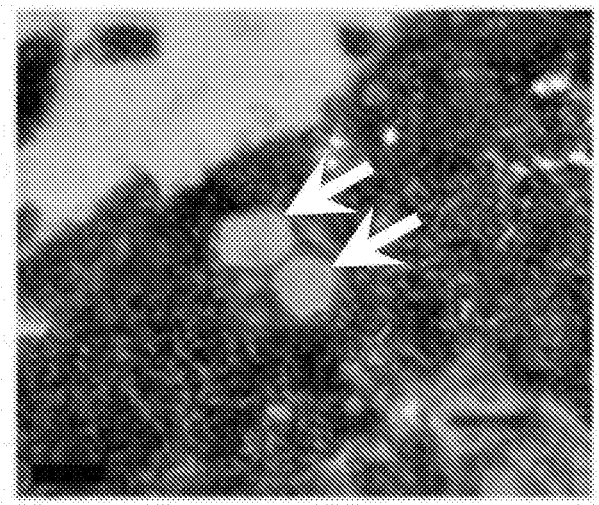

To demonstrate that the human PMPs have a functional role, both DiI-labeled plain liposomes and DiI-labeled PLPs were incubated with murine endothelial cells (SVECs), murine monocytes (RAW264.7), and murine peritoneal macrophages (MΦ) for 4 hours at 37° C. Subsequently, the excess or the unbound DiI-labeled plain liposomes or PLPs were removed, then flow cytometry analysis was conducted. (FIG. 3A). Unlike the plain liposomes, PLPs showed strong binding affinity for RAW264.7 cells but not for SVECs. Due to the phagocytic activity of MΦ, both plain liposomes and PLPs displayed lower DiI signals in MΦ compared to the other two cell types. Additionally, the exposure of PLPs to MΦ resulted in multiple vacuole formation (white arrows, FIG. 3B), in which PLPs could be seen in some of the vacuoles (white arrows, FIG. 3B).

Figure 3D:
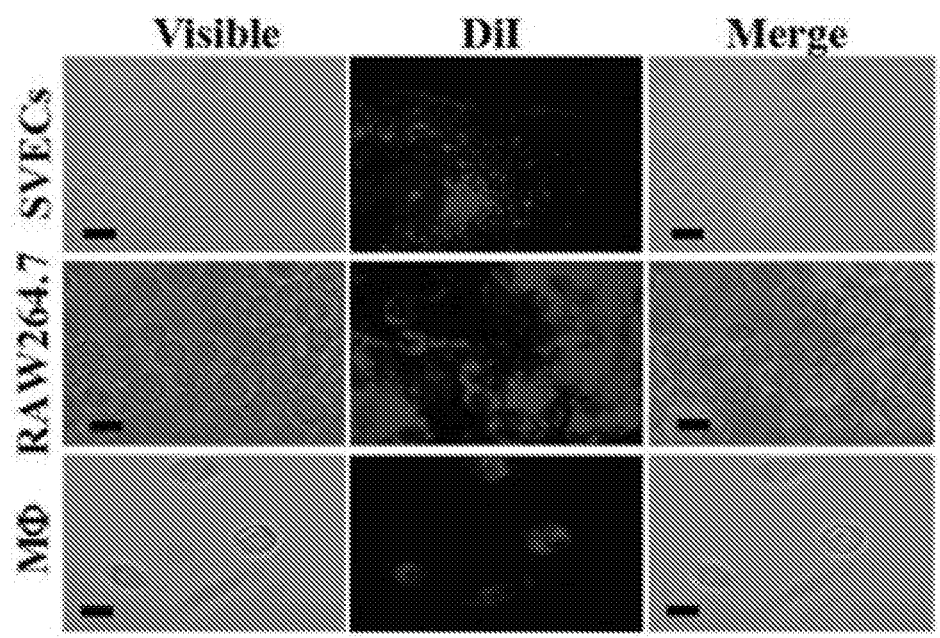
Figure 3E:
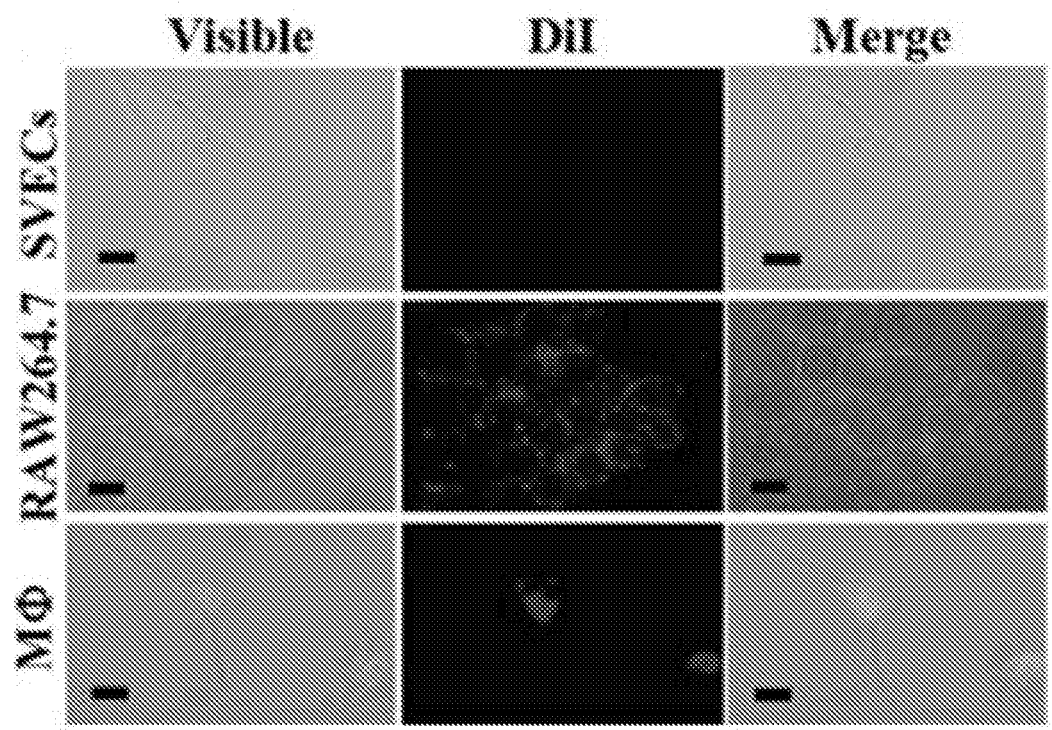

Similar results were also seen in the fluorescence images showing the interactions of the DiI-labeled plain liposomes and PLPs with the three cell types. All three examined cell types had positive interactions with the DiI-labelled plain liposomes (FIG. 3D). In contrast, PLPs showed absolutely no interaction with SVECs, whereas the DiI signals were detected in RAW264.7 and MΦ (FIG. 3E). In contrast to the plain liposomes that were seen aggregating in RAW264.7 cells, the PLPs were notably localized on the surfaces of RAW264.7 cells rather than in the cytosol.

Collectively, these results demonstrated that the presence of human PMPs on PLPs allowed the proteoliposomes to bind to monocytes but not endothelial cells. This characteristic is important as it indicates that PLPs are unlikely to aggregate along the endothelium if intravenously injected, and that PLPs are more likely to adhere to circulating monocytes compared to plain liposomes. Alternatively or in addition, the proteoliposomes described herein may have a low binding activity to platelets and/or red blood cells so as to reduce the risk of inducing blood clotting. Moreover, after 4 hours of exposure, most PLPs localized on the surfaces of RAW264.7 rather than in cytosol, suggesting PLPs are less likely to be phagocytized by circulating monocytes, hence minimizing the chance of premature drug release.

Figure 2A:
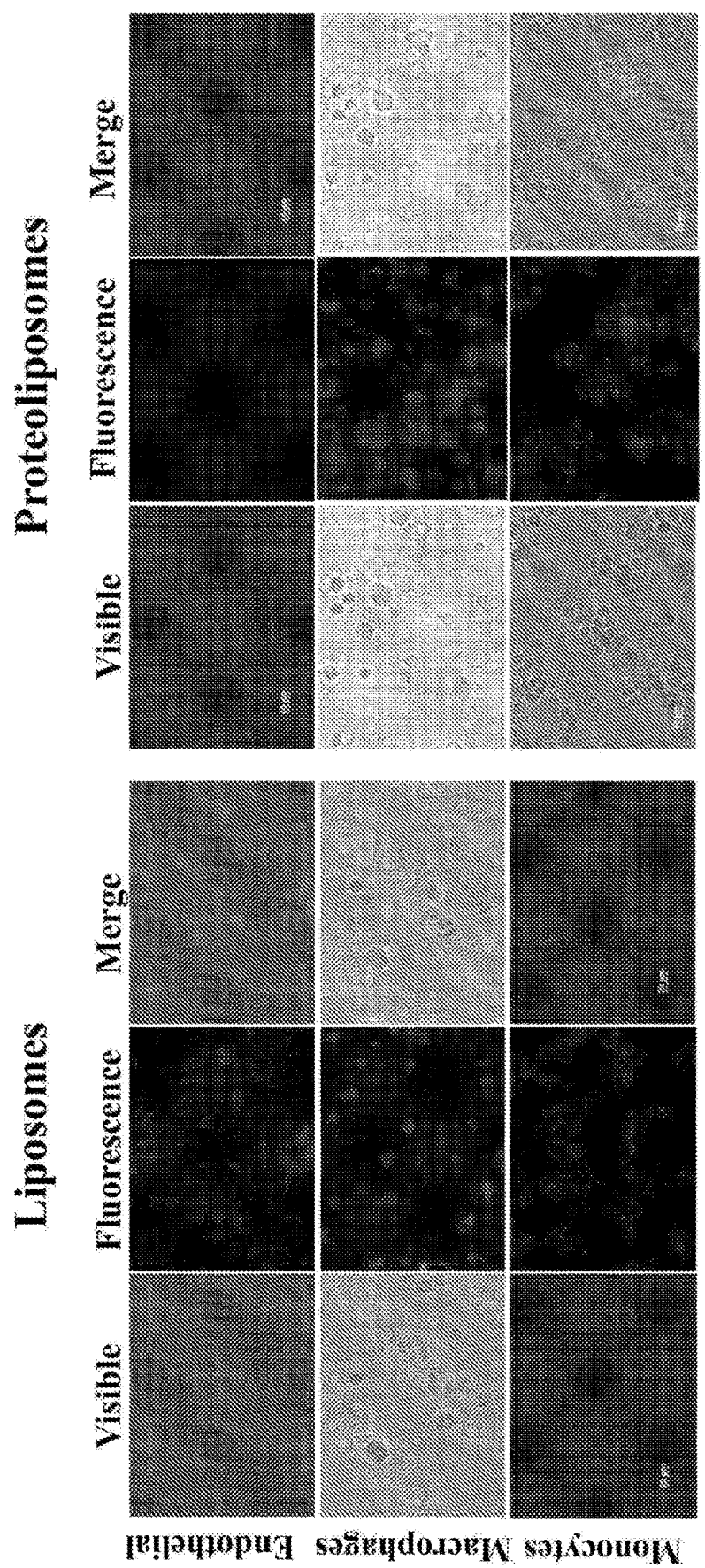
FIGS. 2A-2B are photos showing interactions of platelet-like proteoliposomes with various cell types.
Figure 2B:
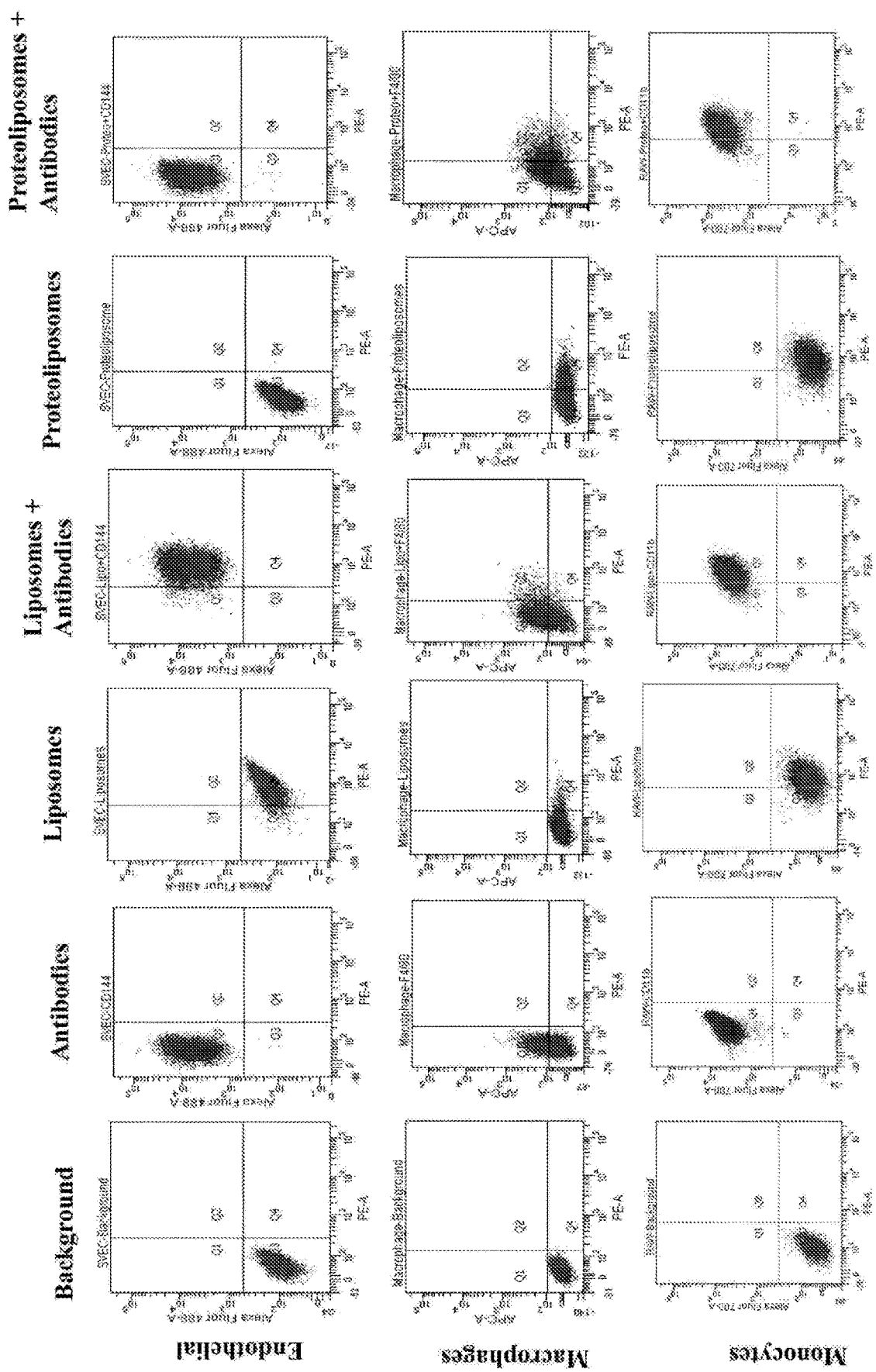

The fluorescence imaging results are shown in FIG. 2A. The DiI-labeled liposomes showed strong binding to endothelial cells, monocytes and macrophages. In contrast, the DiI-labeled platelet-like proteoliposomes only showed positive signals with monocytes and macrophages only. Moreover, fluorescent signals of the platelet-like proteoliposomes were localized inside macrophages, but on membrane surfaces when incubated with monocytes. Thus, the data suggested the platelet-like proteoliposomes have targeting specificity for monocytes and not endothelial cells. Additionally, the platelet-like proteoliposomes localized on the membrane surface of monocytes but localized intracellularly when incubated with macrophages. The same result was also seen by flow cytometric analysis (FIG. 2B).

PLPs Have Better Targeting to the Tissue Injury Site than Plain Liposomes

Figure 4A:
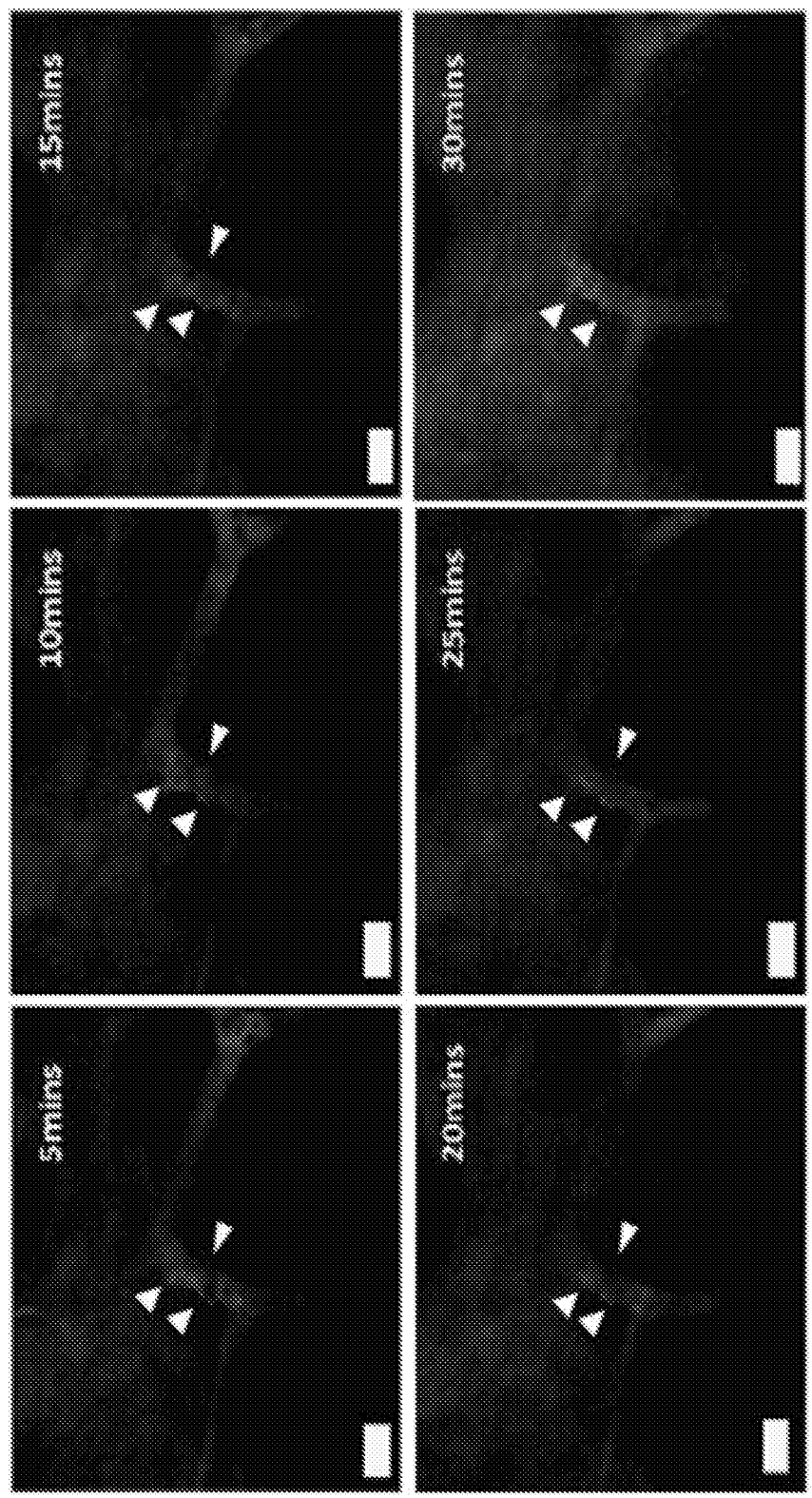
FIGS. 4A-4D show the localization of DiI-labeled PLPs in laser-injured mouse ear skin. After a burn injury was induced in the mouse ear, 100 μL of 5 mg/mL of either DiI-labeled plain liposomes or PLPs (white arrowheads) were injected intravenously. Blood vessels were pre-stained with isolectin antibodies. Multiphoton microscopic lenses were focused at the injury site to capture the 30 minute time-lapse images of the extravasation of plain liposomes (FIG. 4A) and PLPs (FIG. 4B). After 30 minutes filming, five random locations in the peri-injury site were imaged in both plain liposome (FIG. 4C) and PLP-treated (FIG. 4D) mice; scale bar; 50 μm.
Figure 4B:
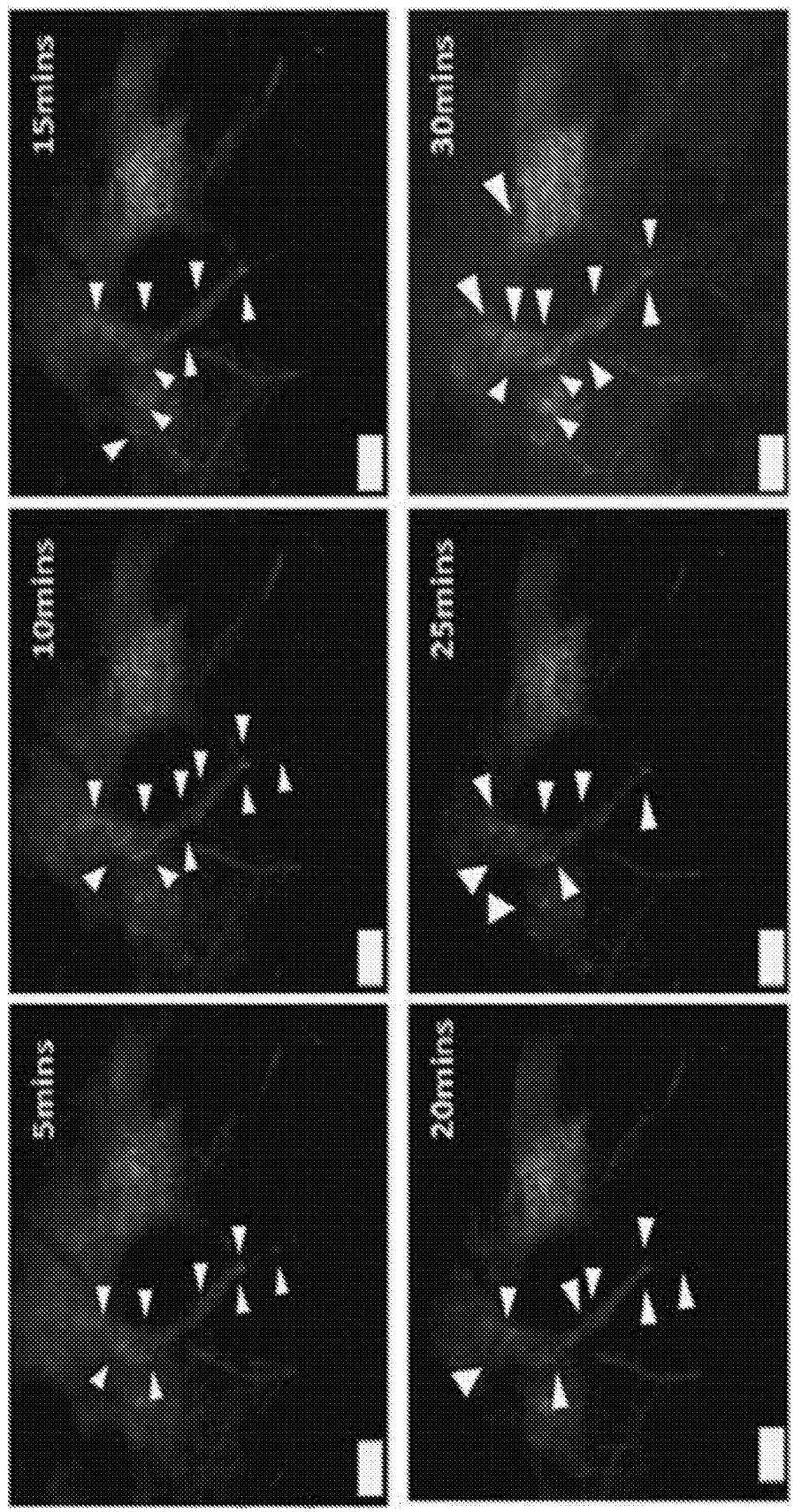
Figure 4C:
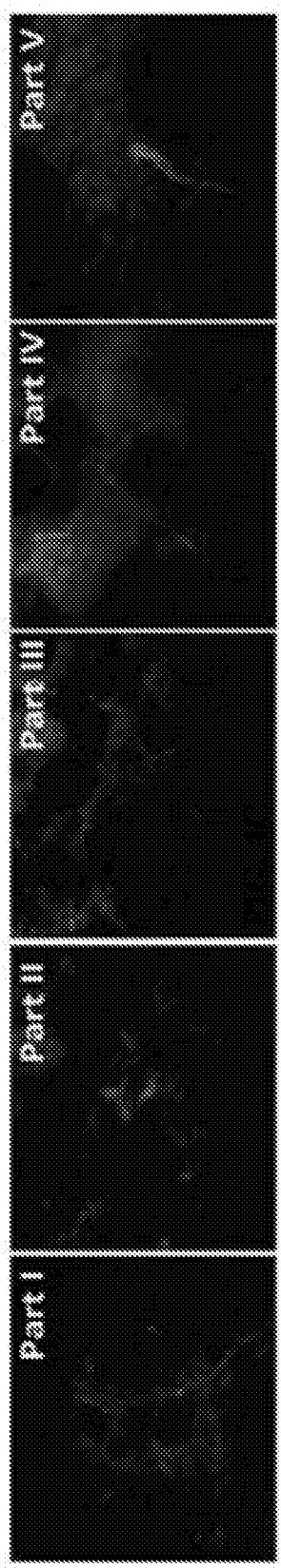
Figure 4D:
Figure 9:
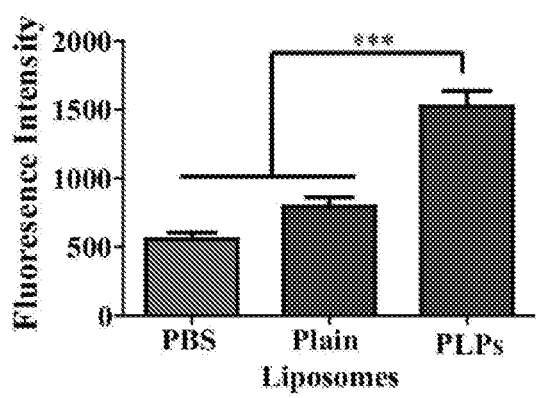
FIG. 9 shows the statistical analysis of detected DiI+ signals in laser-induced injured area at 30 minutes post-injection. The total fluorescence signals of DiI-labeled plain liposomes or PLPs detected at the laser-induced injury site of a mouse ear were measured and statistically analysed (n=3). ***, P<0.001.

Since the inflammatory responses in wound healing are similar to those seen in CHD patients, the targeting profile of the plain liposomes and the PLPs was examined in vivo using laser-induced mouse ear tissue injury as a model. After the injury was created, the mouse was allowed to rest for approximately 48 hours, followed by an intravenous injection of either DiI-labeled plain liposomes or PLPs through the tail vein of the mouse. Upon injection, the microscopic lens of two-photons was focused at the injured area to capture the images of the two liposomes every 5 minutes for up to 30 minutes. Very few of the injected plain liposomes (white arrowhead, FIG. 4A) were seen at the injured area compared to the mouse injected with PLPs (FIG. 4B). After creating a 3D rotating image from the images collected at the 30 minute time point, it was noticed that a huge amount of DiI-labeled PLPs had infiltrated into the tissue injury site, whereas very few of the plain liposomes were seen at the injured tissue. When visualizing vessels that were not at the injured area at the 30 minute time point, it was noticed that there was a large amount of DiI-labeled plain liposomes (FIG. 4C). In contrast, very few of the DiI-labeled PLPs were detected in areas outside the injury site (FIG. 4D). Mice injected with PLPs showed significantly higher DiI signals at the injury site compared to those treated with either PBS or the plain liposomes (FIG. 9). In conclusion, the intravital multiphoton imaging data demonstrated that the PLPs have better targeting to the injury site compared to the plain liposomes, which is likely through piggy-backing on the recruited monocytes.

PLPs Displayed Better Targeting to Ischemia/Reperfusion (I/R) Injured Hearts

Figure 5A:
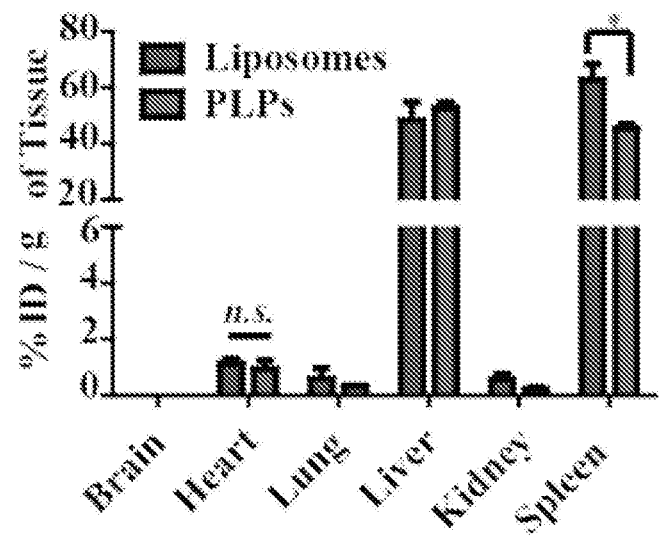
FIGS. 5A-5F show the tissue distribution of PLPs in a murine model of myocardial I/R injury. Ten week-old mice were subjected to 45 minutes of ischemia, immediately followed by 24 (FIG. 5A) or 72 (FIG. 5B) hours reperfusion. Either liposomes or PLPs were intravenously injected, and were allowed to circulate tor 4 hours before sacrifice. Collected organs were perfused and homogenized for subsequent HPLC analysis. n=6, *, P<0.05. , P<0.01.
Figure 5B:
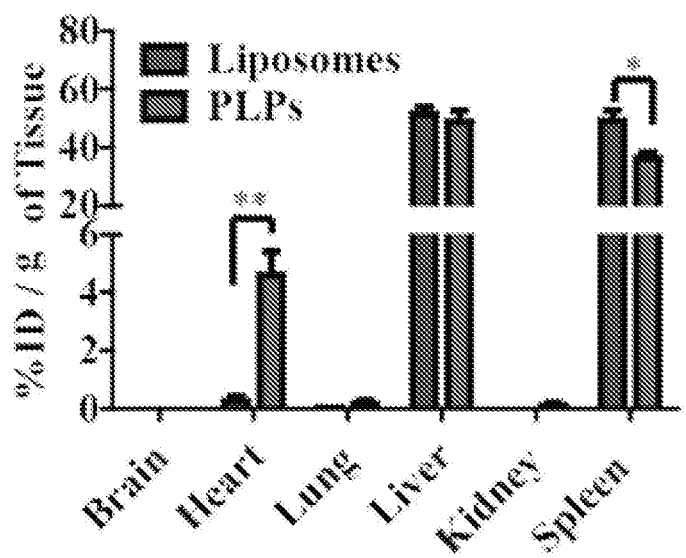

To demonstrate that PLPs can be clinically applied to coronary heart disease (CHD) patients, the tissue distributions of the plain liposomes versus PLPs were investigated in a murine model of I/R injury. The mice underwent 45 minutes of surgically-induced ischemia followed by reperfusion. Since it has been demonstrated in human CHD patients that the number of monocytes recruited to the infarcted heart peaked at 72 hours post-infarction (van der Laan et al., (2014) Eur Heart J 35:376-385), 100 µL of 5 mg/Kg of either the DiI-labeled plain liposomes or PLPs were injected into mice after either 24 hours or 72 hours reperfusion. Subsequently, both the plain liposomes and PLPs were allowed to circulate for 4 hours before the mice were sacrificed and the level of DiI signals in the organs were subjected to HPLC analysis (FIGS. 5A and 5B).

Figure 5C:
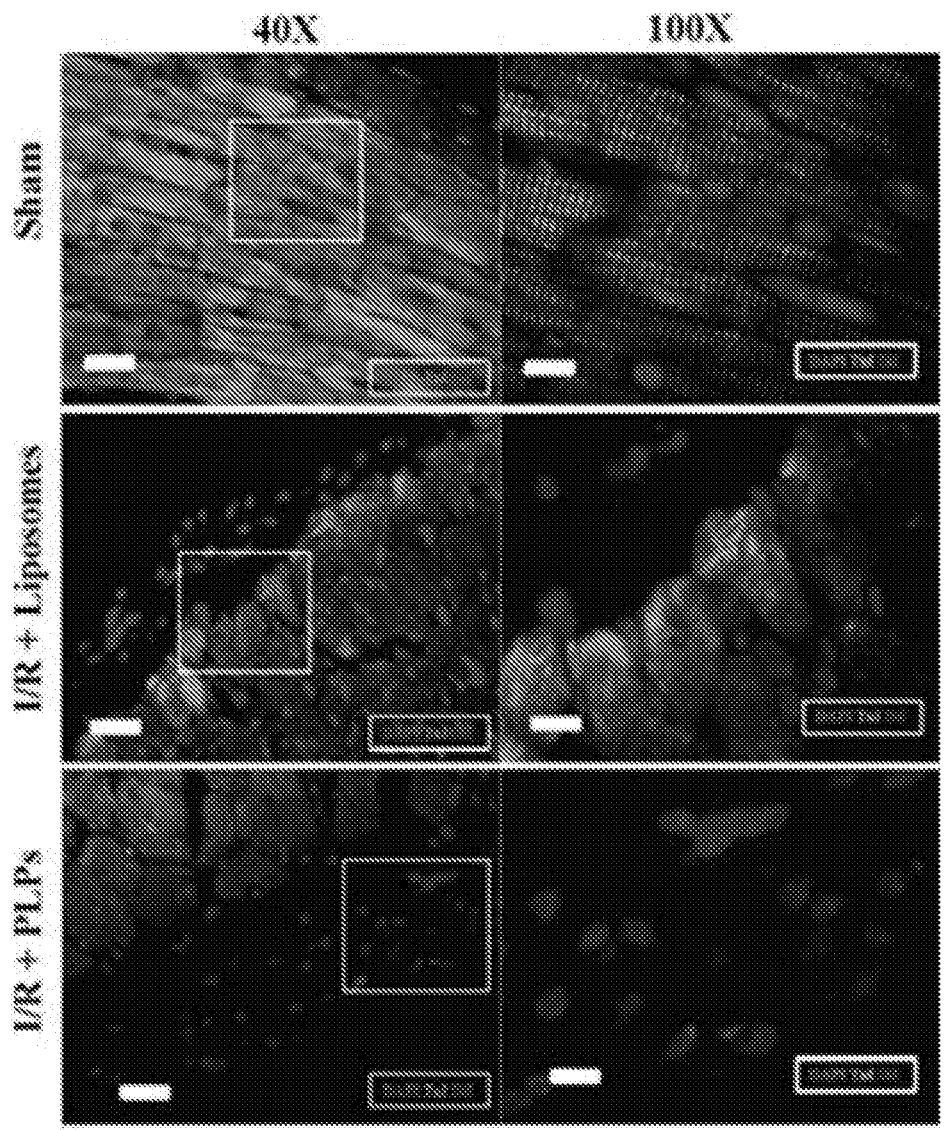

When the mice were administered with either the plain liposomes or PLPs at 24 hours of reperfusion, the brain did not show any positive DiI detection for either lipid material. Minimal levels were detected in the heart, lung and kidney, although there was no significant difference between detection in the plain liposomes and PLPs. The liver and spleen were the two major organs that showed highest DiI signals for both the plain liposomes and PLPs. Interestingly, the detections of PLPs were significantly less in the spleen compared to the plain liposomes, suggesting the human PMPs on PLPs may play a role in preventing PLPs from getting trapped in the spleen. A similar distribution profile was also seen when either the DiI-labeled plain liposomes or PLPs were intravenously injected at 72 hours of reperfusion, with the exception of the heart. Remarkably, a significant difference was not only seen in the spleen, as PLPs also showed an elevated response in the heart compared to the plain liposomes, indicating that the presence of PMPs on PLPs leads to better targeting of the infarct heart. The presence of PLPs in the infarcted heart was also detectable in the sectioned heart tissue that had PLPs administered at 72 hours of reperfusion (FIG. 5C). Unlike the sham group, the full intact sarcomere structure could not be seen in the I/R injured heart in either the DiI-labeled plain liposome-treated or PLP-treated groups. However, the fluorescence signals of the PLPs were clearly seen in the infarct area, whereas there was no visible detection with the plain liposome-treated heart sample.

Figure 5D:
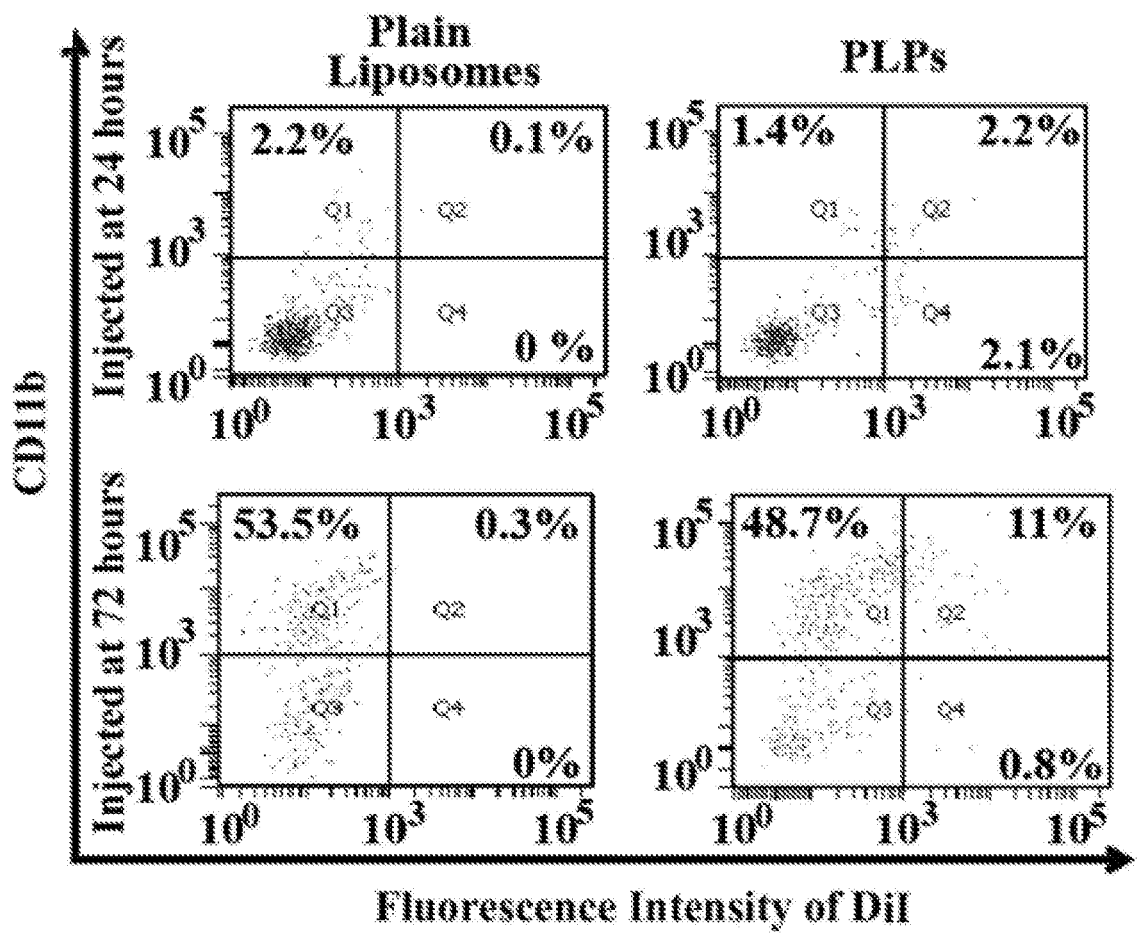
Figure 5E:
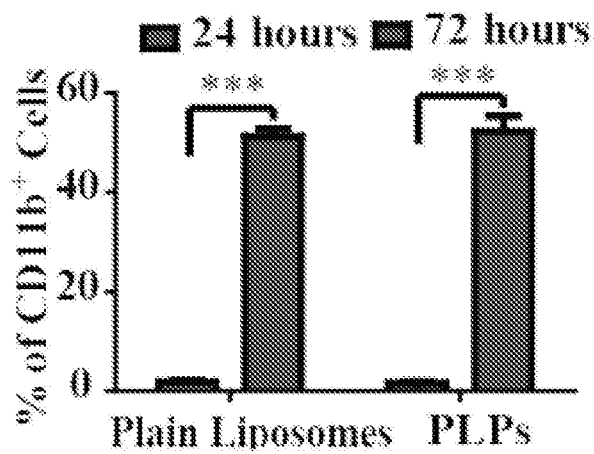
Figure 5F:
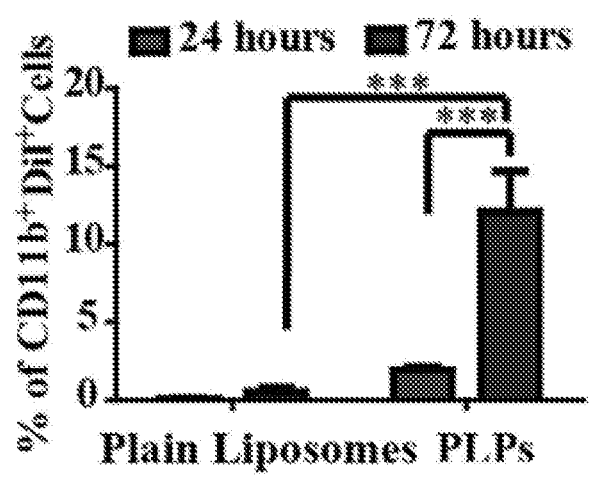

To demonstrate the transportation of PLPs into the injured myocardium is indeed monocyte-mediated, the numbers of infiltrated monocytes in the whole hearts were determined by flow cytometry (FIG. 5D). Hearts from mice sacrificed at 24 hours of reperfusion showed very little of CD11b$^+$ in both the plain liposome and the PLP-treated groups. In contrast, mice sacrificed at 72 hours of reperfusion showed a significant increase of CD11b$^+$ cells in the injured hearts (FIG. 5E). Furthermore, the numbers of CD11b$^+$ DiI$^+$ cells in the hearts were significantly higher in PLP-treated mice that were administered at 72 hours of reperfusion compared to those administered at 24 hours of reperfusion (FIG. 5F). The same effect was not seen with the mice that were administered plain liposomes at 24 or 72 hours reperfusion. Therefore, the data indicated when injected at 72 hours of reperfusion, a significant amount of PLPs infiltrated the injured myocardium, and that the infiltration is monocyte-mediated.

Figure 10A:
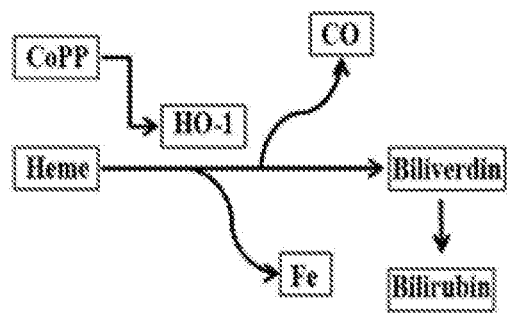
FIGS. 10A-10C show in vitro analysis of CoPP-induced expression of HO-1.

Treatments with PLP-Encapsulated Cobalt Protophorphyrin IX (CoPP) Reduced the Infarct Area of the Heart Cobalt protoporphyrin IX (CoPP) is a small molecule that is known to suppress the inflammatory activity of macrophages through induction of heme oxyenase-1 (HO-1) expression (FIG. 10A). HO-1 catalyzed the breakdown of heme into biliverdin, carbon monoxide (CO) and iron. CO, biliverdin, and the final heme catabolic end-product, bilirubin, are known to have strong anti-oxidant and anti-inflammatory activities (Zhao et al., (2013), PLoS One 8:e75927), and the by-product iron has been demonstrated to participate in ferritin synthesis, in which ferritin has anti-apoptotic activity (Zhao et al., (2013), PLoS One 8:e75927). Treatment with CoPP has been shown to significantly reduce the infarct area of the heart. Sodhi et al., (2015), J Cardiol Ther 2:291-301; Cao et al., (2012) Front Physiol 3:160; Chen et al., (2013) Int J Mol Sci 14:2684-2706. Therefore, whether a similar therapeutic effect could be seen with the intravenously injected PLP-encapsulated CoPP (PLP–CoPP) in a murine model of I/R injury was investigated.

Figure 10B:
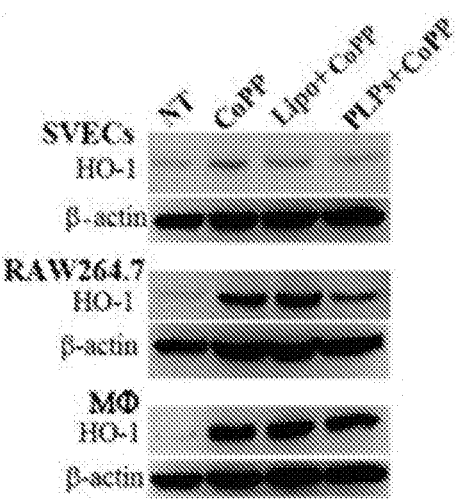
Figure 10C:
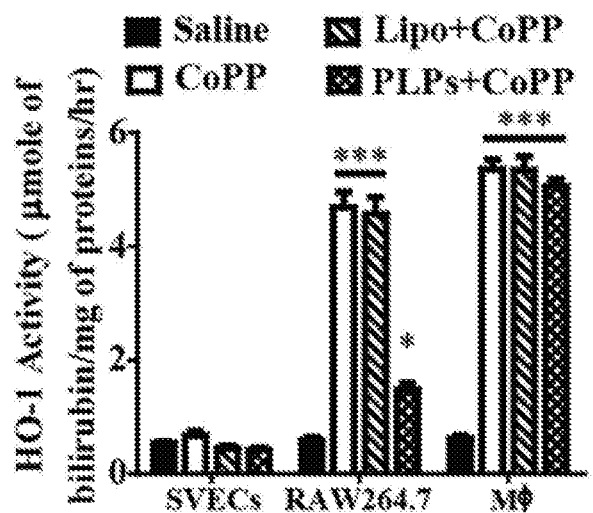

The capability of PLP–CoPP to induce HO-1 expression was first investigated in SVECs, RAW264.7 cells and MΦ (FIG. 10B). Compared to β-actin expression, the exposure to either plain liposome-encapsulated CoPP (Lipo–CoPP) or PLP–CoPP did not result in any significant HO-1 expression in SVECs, although treatment of free CoPP did seem to result in the induction of some expression. In contrast, treatment with either free CoPP or Lipo–CoPP induced strong HO-1 expression compared to the untreated control. Although the HO-1 expression in the RAW264.7 cells treated with PLP–CoPP was stronger than the non-treated control, the band was less intense compared to either the free CoPP or the Lipo–CoPP treatments. Therefore, the data suggests that, unlike the Lipo–CoPP, the human PMPs on the surfaces of PLPs prevent the encapsulated CoPP from being easily taken up by the cells. Compared, to SVECs and RAW264.7 cells, strong HO-1 expression was seen in all forms of the CoPP-treated MΦ. Moreover, by measuring the level of bilirubin in an in vitro activity assay, it was demonstrated that all the CoPP-induced expression of HO-1 was enzymatically active (FIG. 10C). In addition, the enzyme activity of HO-1 in each corresponded to the expression level of enzyme in each of the CoPP-treated samples.

Figure 6A:
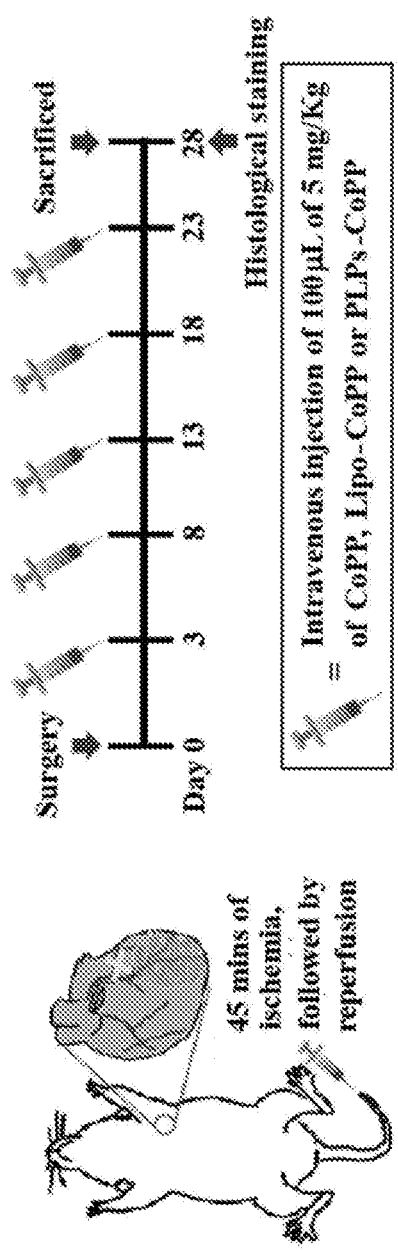
FIGS. 6A-6D show therapeutic analysis of PLP–CoPP in a murine model of myocardial I/R injury.
Figure 6B:
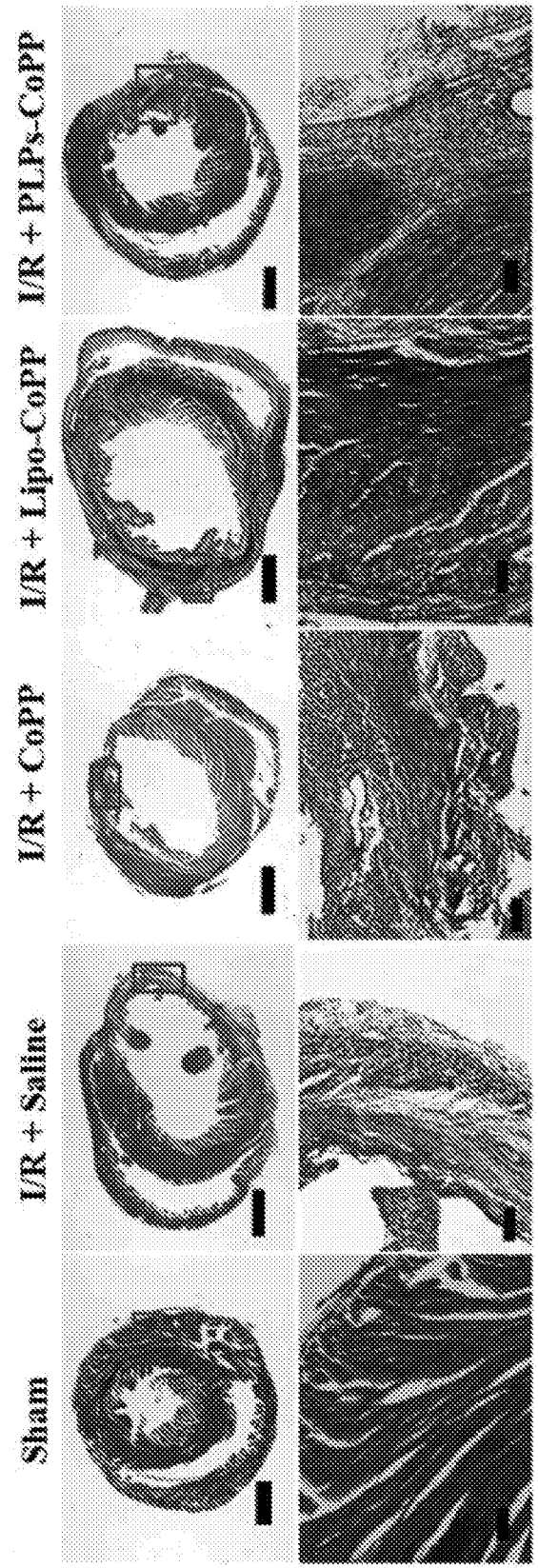
Figure 6C:
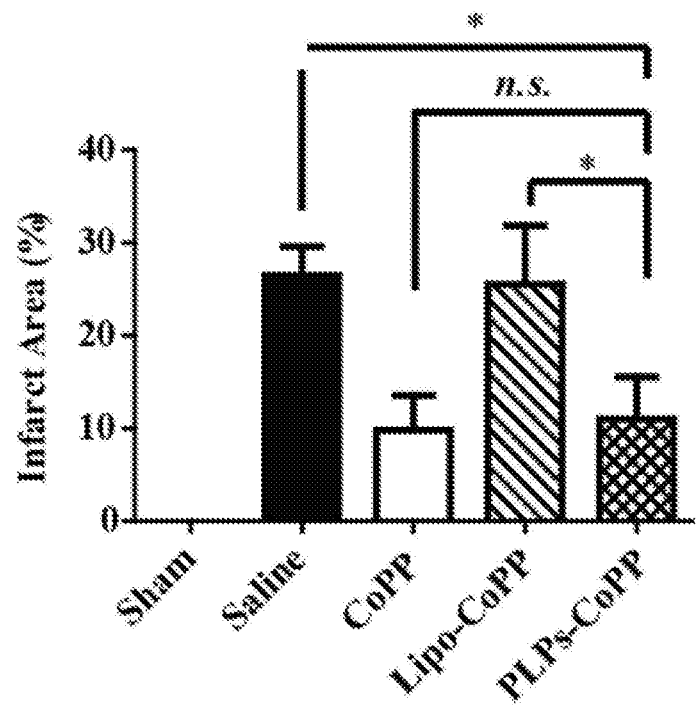

Prior to conducting the experiment investigating the capability of PLP–CoPP to reduce the infarct area of the heart in a murine model of I/R injury, the stability of the encapsulated CoPP in plain liposomes and PLPs was examined (Table 5). As opposed to Lipo–CoPP, the DLS measurements showed that there was no difference in the encapsulation efficiency of PLP–CoPP at 3 days compared to the immediate measured values. Furthermore, there was no change in the size of PLP–CoPP at 3 days after the initial encapsulation. But, from 7 days onward, significant reductions in the CoPP loading were seen for both Lipo–CoPP and PLP–CoPP. Hence, for all subsequent animal experiments, Lipo–CoPP were prepared one day before an in vivo experiment, whereas PLP–CoPP were freshly prepared 3-4 days before an experiment.

group, the mice treated with Lipo–CoPP did not show much improvement in reducing the infarct area, whereas significant reduction was seen in the mice treated with either free CoPP or PLP–CoPP (FIG. 6C). These results demonstrated that the encapsulation of CoPP by PLPs did not reduce the therapeutic benefit of the drug. Furthermore, the fact that the CoPP encapsulated in the plain liposomes failed to exert any therapeutic effect on the infarcted heart, is a clear indication of the important role that the conjugated human PMPs play in targeting the encapsulated drug to the infarcted heart.

Figure 6D:
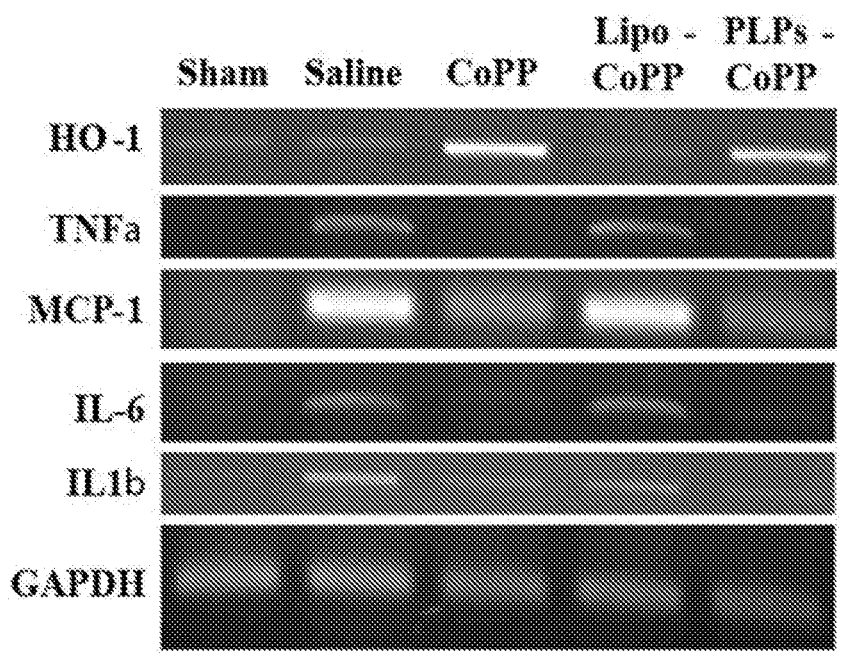

Treatments of CoPP or PLPs–CoPP were shown to downregulate several pro-inflammatory genes in the I/R injured hearts (FIG. 6D). Intravenous injection of either CoPP or PLPs–CoPP upregulated the expression of the HO-1 gene (HMXO1) in the hearts of treated mice compared to the saline and Lipo–CoPP treated mice. In comparison, the pro-inflammatory genes such as TNFα, MCP-1, IL6 and IL1β were downregulated in the CoPP and PLPs–CoPP treated groups. Thus, the results indicated that either CoPP or PLPs–CoPP could induce HO-1 expression in I/R injured hearts, and that HO-1 exerted its anti-inflammatory effect, resulting in the downregulation of several pro-inflammatory cytokines.

PLPs Minimize the Adverse Effect of CoPP

Although the therapeutic benefits of CoPP in animal models of MI are well-documented, its undesired off-target effects have also been reported. Schmidt, (2007), FASEB J 21:2639; Ryter et al., (2006) Physiol Rev 86:583-650. To evaluate the overall efficacy of PLP–CoPP, the cardiac functions in a murine model of non-reperfused MI was first examined after the PLP–CoPP treatment. Once ischemia was surgically induced, the mice were intravenously injected with 100 µL of 5 mg/mL of free CoPP, Lipo–CoPP or PLP–CoPP at 3 days post-infarction. Subsequently, the

TABLE 5

Quantification of CoPP Encapsulated in PLPs

| | Z-average (nm) | Drug-to-lipid weight ratio | Encapsulation efficiency (%) |
|---|---|---|---|
| Liposomes | | | |
| Immediately after encapsulation | 124.9 ± 2.17 | 3:1 | 90.74 ± 1.65 |
| 3 days after encapsulation | 176.63 ± 3.25 | 3:1 | 81.38 ± 2.48** |
| 7 days after encapsulation | 306.93 ± 8.46 | 3:1 | 63.75 ± 3.21*** |
| 14 days after encapsulation | 481.6 ± 1.44 | 3:1 | 35.57 ± 10.08*** |
| Platelet-like Proteoliposomes (PLPs) | | | |
| Immediately after encapsulation | 119.2 ± 0.95 | 3:1 | 90.42 ± 1.82 |
| 3 days after encapsulation | 119.33 ± 1.27 | 3:1 | 90.45 ± 0.97 |
| 7 days after encapsulation | 189.47 ± 5.50 | 3:1 | 76.57 ± 3.28** |
| 14 days after encapsulation | 220.867 ± 1.76 | 3:1 | 52.65 ± 8.05*** |

Three batches of cobalt protoporphyrin IX (CoPP) encapsulated in either liposomes or PLPs (n = 3) were subjected to dynamic laser scattering analysis to determine the size of the particles after encapsulation. The encapsulation efficiency of CoPP in either liposomes or PLPs at different incubation time was determined by HPLC.
P < 0.01, *P < 0.001, vs. the immediate measurements of the encapsulation efficiency of CoPP in either plain liposomes or PLPs.

Figure 7A:
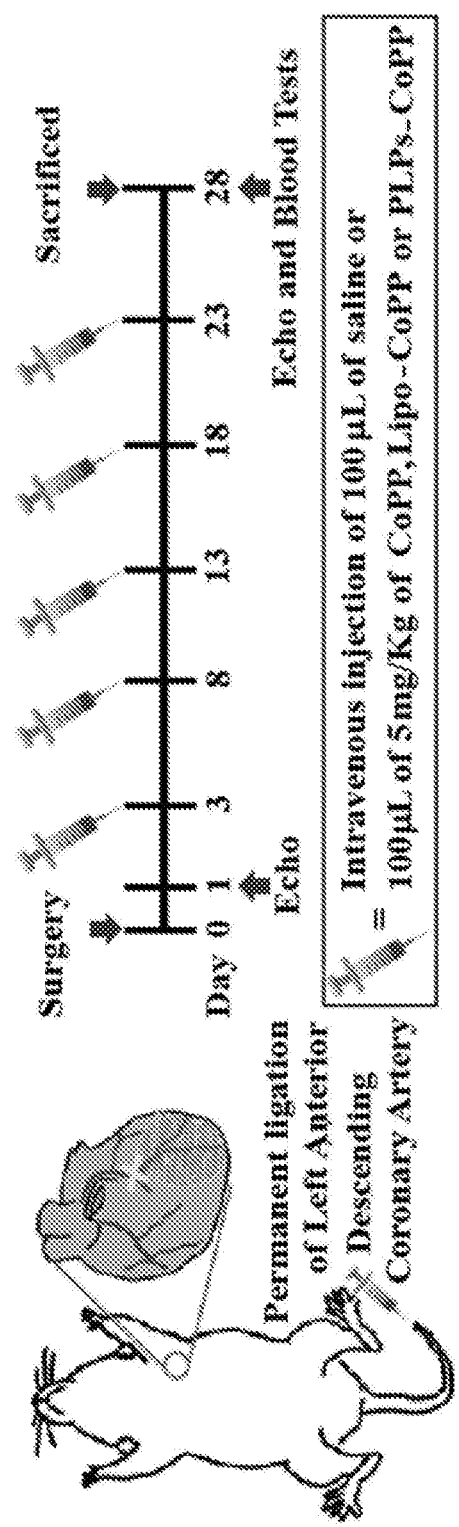
FIGS. 7A-7D show echocardiographic assessments of cardiac function and blood chemistry analysis of a murine model of MI injury after PLP–CoPP treatments.
Figure 7B:
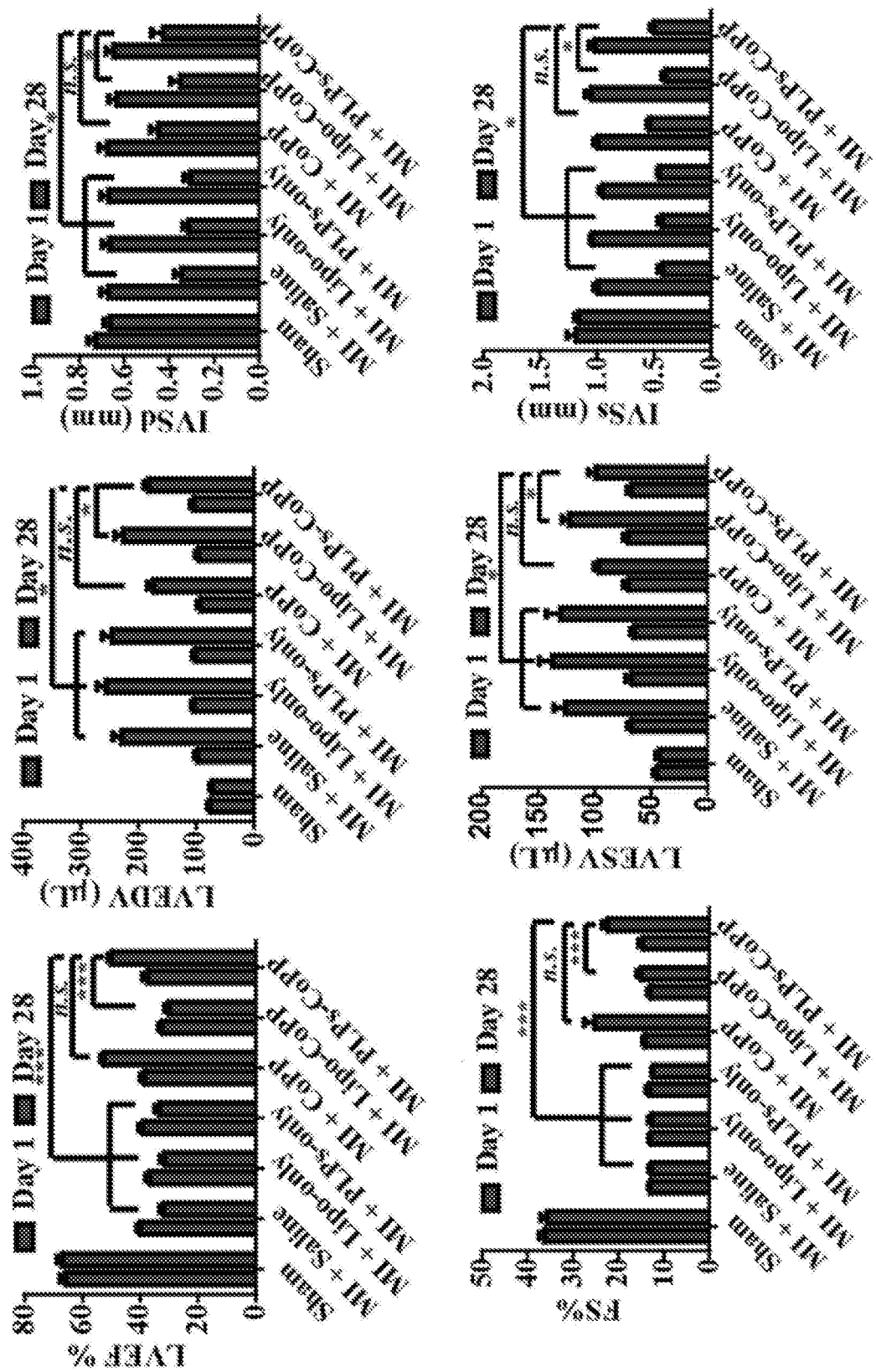
Figure 11:
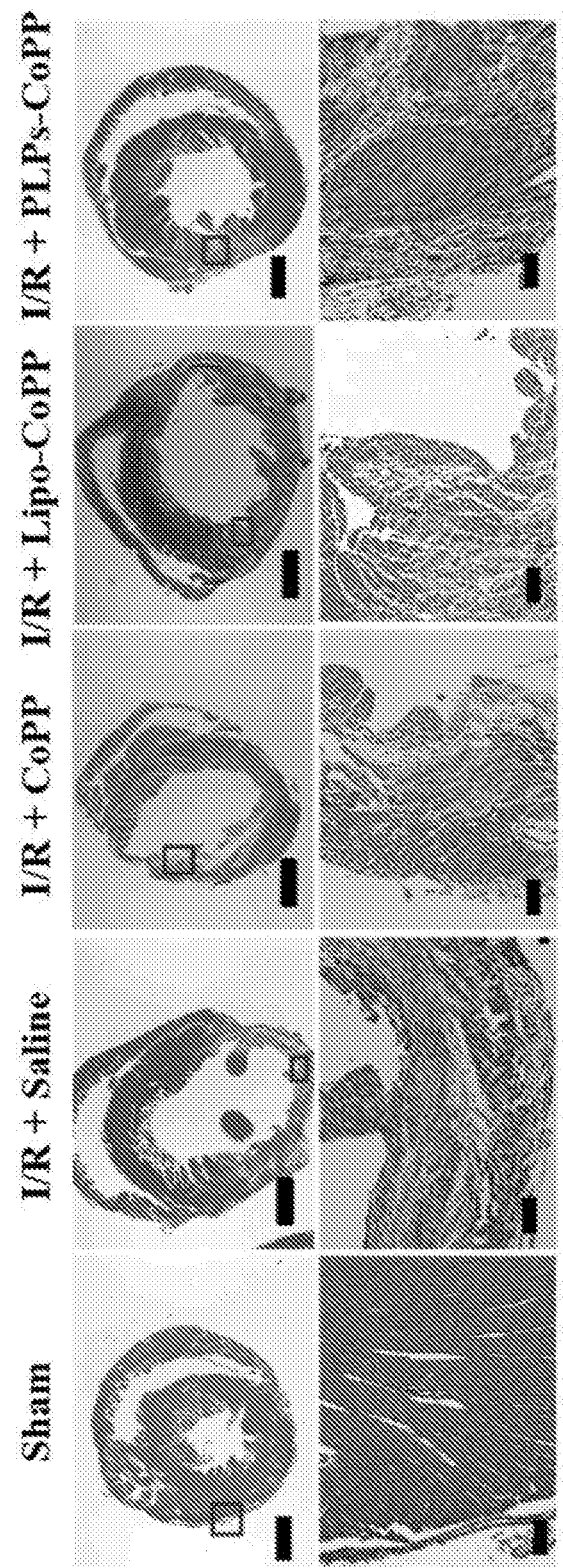
FIG. 11 shows hematoxylin and eosin staining of sectioned heart tissues. Infarct area in the hearts of murine models of I/R injury (n=4) was accessed by hematoxylin/eosin (H&E). Scale bar; 1 mm for the whole section and 100 μm for the higher magnified images. The mice were subjected to 45 minutes of ischemia and 72 hours of reperfusion, followed by intravenous injection of saline, CoPP (5 mg/Kg), Lipo–CoPP (5 mg/Kg) or PLP–CoPP (5 mg/Kg). Subsequent injections were made every 5 days until day 28, in which the mice were sacrificed.

A previous pharmacokinetic study of CoPP in mice has shown 5 mg/kg of CoPP for every 5 days is sufficient to induce strong expression of HO-1 in vivo. Chen, et al., (2013), Int J Mol Sci 14:2684-2706. After the mice were subjected to 45 minutes of ischemia and approximately 72 hours of reperfusion, 100 µL of 5 mg/Kg of free CoPP, Lipo–CoPP or PLP–CoPP was injected through the tail vein (FIG. 6A). The same dosage was then administered every 5 days until 21 days following reperfusion, and then the mice were sacrificed and the hearts were harvested for histological analysis (FIGS. 6B and 11). Compared to the I/R+saline mice were administered with the same dosage every 5 days until 28 days post-infarction (FIG. 7A). The cardiac functions of the mice in all treatment groups were accessed by echocardiography at 28 days post MI (FIG. 7B). The percentage of left ventricular ejection fraction (LVEF, %), which measures the amount of blood that leaves the heart each time it contracts, in the MI PLP–CoPP group was significantly higher than the MI+Saline, MI+Lipo–CoPP, and the two vehicle-alone groups. No significant difference was seen between the MI+CoPP and the MI+PLP–CoPP groups. A similar result was also seen in the measurement of the percentage of fractional shortening (FS %), which is affected by myocardium thickness; those treated with PLP–CoPP showed significant improvement in FS % compared to the other treatment groups, except for the MI+CoPP group. The volume of blood in the ventricle at the end of the diastole (LVEDV) and systole (LVESV) were also evaluated for all the groups. Although, the treatments of either free CoPP or PLP–CoPP did not lower LVEDV and LVESV to the same level as seen in the sham group, the results were still significantly better than the other treatment groups. Likewise, the intraventricular septal width measured at the diastole (IVSd) or systole (IVSs) further indicated that PLP–CoPP improved the overall cardiac function of the mice in a similar manner to the free CoPP treatments.

Figure 7C:
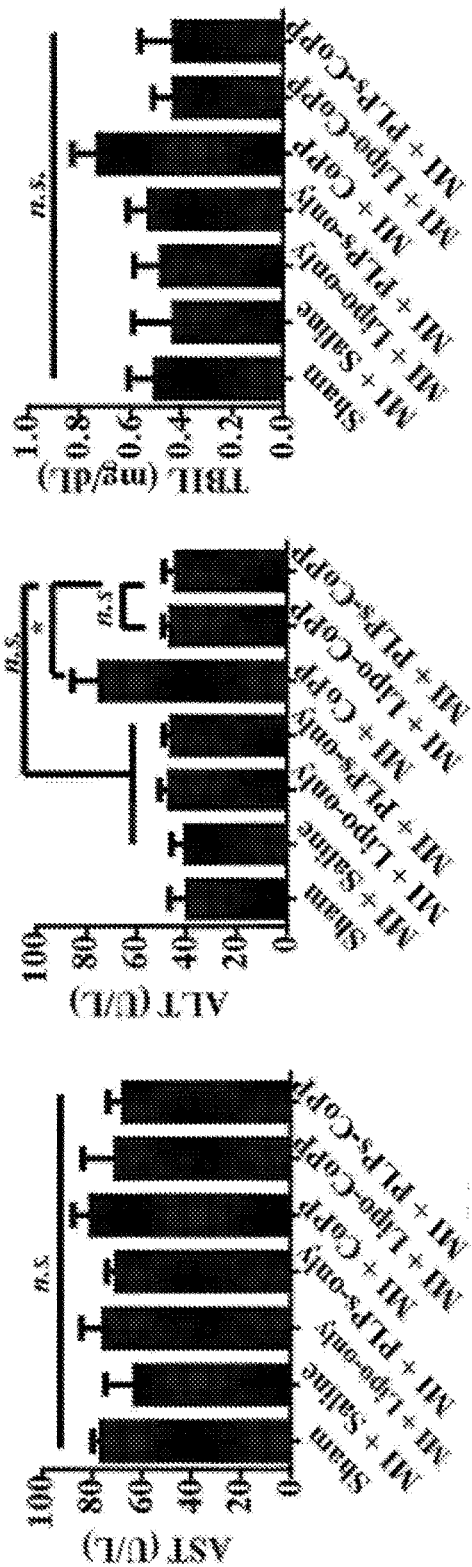
Figure 7D:
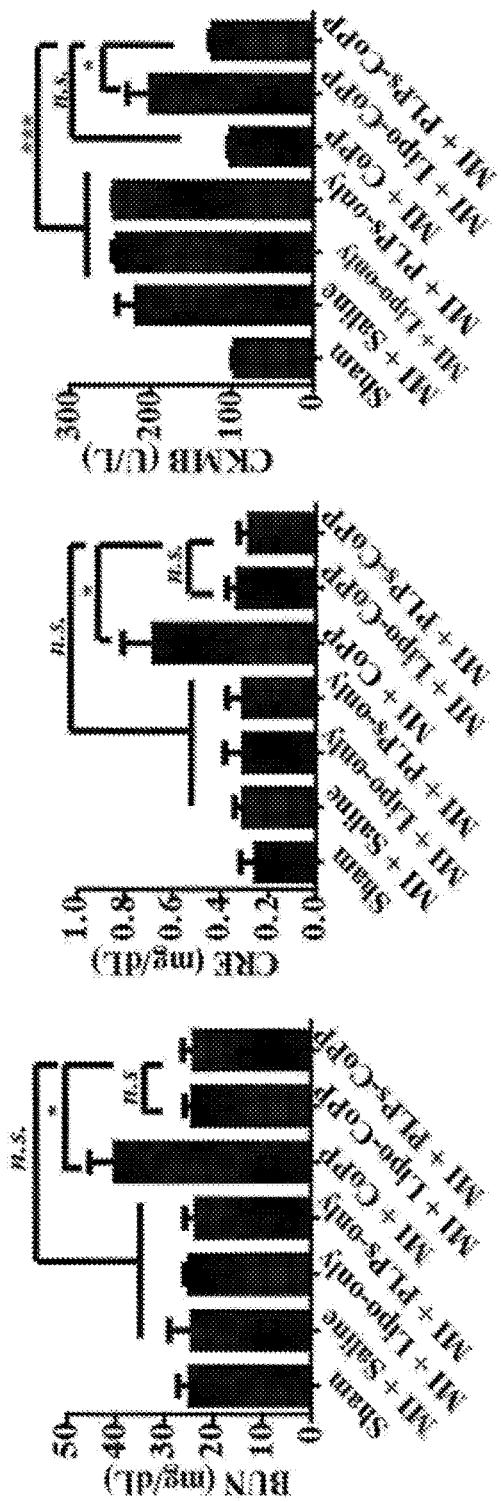

Next, to determine the capability of PLPs to minimize the off-target effects of CoPP on other organs, serum analysis was conducted on the blood of all the treatment groups at the end of the 28-day treatment (FIGS. 7C-7E). Levels of aspartate transaminase (AST), alanine transaminase (ALT), and total bilirubin in the serum were the biomarkers used to evaluate the hepatotoxicity of CoPP (FIG. 7C). There was no significant difference in the AST and TBIL measurements among the treatment groups. However, a significantly higher level of ALT was detected in the MI+CoPP group compared to the MI+PLP–CoPP group. Moreover, the MI+Lipo-CoPP and the MI+PLP–CoPP groups both showed a similar ALT level to the sham group. Similar results were also seen in the measured serum level of blood urine nitrogen (BUN) and creatinine (CRE), which are biomarkers for renal toxicity (FIG. 7D). It was clear that neither the Lipo–CoPP nor the PLP–CoPP treatment enhanced the serum level of either BUN or CRE like the CoPP treatments did. Measurements of the serum level of creatine kinase MB (CKMB), a biomarker of cardiotoxicity, showed that both the MI+CoPP and the MI+PLP–CoPP groups had significantly lower CKMB levels compared to other treatment groups (FIG. 7E). This indicated that CoPP itself did not induce any additional cardiotoxicity, and that any elevated level of CKMB is likely the result of ischemic injury.

Figure 8:
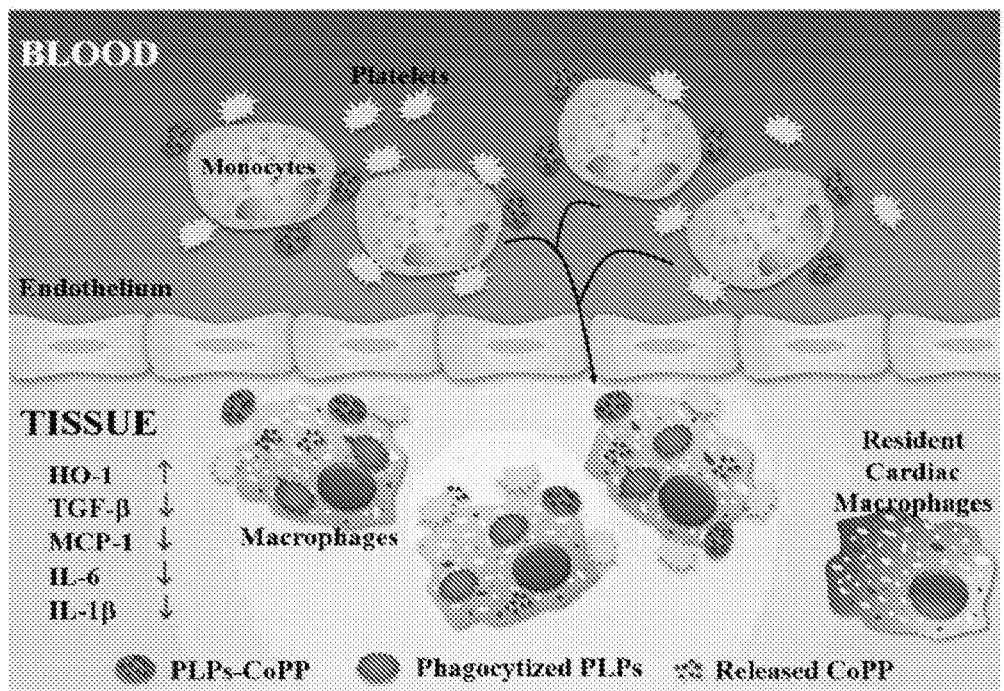
FIG. 8 shows that PLPs enhance the targeting specificity of CoPP through biomimicking platelet interactions with circulating monocytes. The binding of PLPs with circulating monocytes provides an alternative route for delivering a cardioprotective drug such as CoPP in an EPR effect-independent manner. Once the recruited circulating monocytes infiltrate the injured tissue area, the anchored PLPs are phagocytized by the monocyte-derived macrophages. Upon phagocytosis, the encapsulated CoPP will be released into the cytosol and induce HO-1 expression, which downregulate the expression of pro-inflammatory cytokines. Moreover, not only PLPs minimized the adverse effects of CoPP on other organs, the delivery vehicle is likely to minimize the chance of CoPP come in contact with the resident cardiac macrophages.

Taken together, the results of the present study demonstrated that the PLPs described herein effectively delivered CoPP to the injured areas in heart and minimized the side effect associated with off-target delivery of Copp. This process is illustrated in FIG. 8.

Discussion

Transferring the promising bench results of potential cardioprotective drugs to the clinic remains a challenging task. Despite continued investment over the past decades, there are still no effective cardio-protective drugs commercially available. Altamirano et al., (2015), J Physiol 593: 3773-3788; Perricone et al., (2014), Pharmacol Res 89:36-45; Sluijter et al., (2014), Pharmacol Ther 144:60-70. Some poor clinical outcomes have been attributed to the use of inappropriate animal models and the individual lifestyles of human patients. However, maximizing the targeting specificity of a systemically delivered drug also remains an unmet need. For example, metformin, a US FDA approved anti-diabetic drug for treating type II diabetes, has been shown to have cardio-protective effects in several animal models. Whittington et al., (2013), Cardiovasc Drug Ther 27:5-16. However, a recent clinical trial that pretreated CHD patients with metformin during coronary artery bypass surgery failed to result in any significant reduction in myocardial injury. El Messaoudi et al., (2015), Lancet Diabetes Endocrinol 3:615-623. Furthermore, patients in the metformin-treated group had a significantly higher occurrence of diarrhea and other gastrointestinal discomfort compared to the placebo group. Thus, the clinical result demonstrated that metformin not only lost its cardio-protective function but also induced adverse effects in the treated patients. Although several reported drug delivery systems claimed to be actively delivered to the infarcted heart, the functionalized surfaces on these delivery systems only allowed them to be better retained at the targeted site and/or enhance their circulation half-life. Dvir et al., (2011), Nano Lett 11:4411-4414; Yan et al., (2014), Biomaterials 35:1063-1073; Chang et al., (2013) J Control Release 170:287-94; Nguyen et al., (2015) Adv Mater 27:5547-5552. These delivery systems still rely on the EPR effect as the main route to reach the target site. Several reports and clinical studies have now indicated that the EPR effect is no longer a dependable strategy for drug delivery, including for cancer therapy. Nichols et al., (2014) J Control Release 190:451-464. Therefore, the monocyte-mediated delivery strategy disclosed herein represents a truly active form of drug delivery.

The monocle-mediated strategy has been previously reported for the delivery of cancer drugs. However, the reported delivery vehicles either had functionalized surfaces that are also recognizable by the endothelium (Qin et al., (2015), Nanomedicine 11:391-400), had unfunctionalized surfaces to facilitate better phagocytosis by the circulating monocytes (Nagaoka et al., (2015), PLoS One 10:e0132451; Afergan et al., (2008), J Control Release 132:84-90), or required the delivery vehicles to be pre-mixed with an external source of monocytes before being systemically delivered. Anselmo et al., (2015) J Control Release 199:29-36. In contrast, the PLPs described herein were designed to mimic the physiological interactions between platelets and the circulating monocytes at post-infarction. The PMPs on PLPs enable the delivery system to hitchhike on the circulating monocytes that are being recruited to the infarcted heart. At the same time, the proteins are likely to provide physical hindrance against the endothelium, thus preventing any undesired thrombosis. Additionally, PLPs were demonstrated to aggregate on the surfaces of monocytes after 4 hours of exposure, rather than being phagocytized by the cells. Such a characteristic is critical, as early phagocytosis could lead to premature release of the encapsulated drugs, which may induce an unwanted effect.

The exemplary PLP-mediated drug delivery system disclosed in the present study utilized a pure solution of PMPs rather than the entire platelet membranes that includes platelet membrane phospholipids, which are known to play a critical role in promoting platelet coagulation at vascular injury sites. Davi et al., (2007), N Engl J Med 357:2482-2494. Since the aim was to maximize the chances of PLPs attaching to the surfaces of monocytes, the presence of the membrane phospholipids would likely promote undesired coagulation on the endothelium as well as among PLPs themselves. Furthermore, liposomes rather than polymers, were chosen as the core of PLPs as it has been demonstrated that liposomes can encapsulate a wide range of drugs and are more acceptable to the regulatory bodies. Torchilin et al., (2014) Nat Rev Drug Discov 13:813-827. Moreover, if the whole platelet membrane were used, the presence of platelet membrane phospholipids would likely hinder the success of conjugating the human PMPs with the DOPC lipids.

The PLPs described herein may not use a single type or a mixture of defined recombinant proteins for the fabrication; instead, they may include the entire purified mixture of human PMPs. Such PLPs showed a high level of interaction with monocytes, thereby enhancing the drug delivery activity.

It was demonstrated in this study that PLPs could only be detected in the infarcted heart at 72 hours and not at 24 hours of reperfusion. This result was unexpected, as some of the platelet receptors that interact with monocytes are also known to interact with neutrophils, which are recruited to the infarcted heart within 24 hours post infarction in human patients. Hausenloy et al., (2015), N Engl J Med 373:1073-1075. The conjugation process may have induced some modifications to the human PMPs, which resulted in poor affinity to neutrophils. Nevertheless, when intravenously injected at 72 hours of reperfusion, approximately 5% of the total injected PLPs were in the heart as opposed to approximately 0.3% of total injected plain liposomes. Moreover, the increased numbers of PLPs correlated with the increased numbers of monocytes detected in the infarcted heart at 72 hours, suggesting the targeting was monocyte-mediated. Such data correspond to the human clinical data which showed the number of recruited monocytes peaked at 72 hours post-infarction and that the majority were in the infarct area. van der Laan et al., (2014), Eur Heart J 35:376-385.

Based on recent clinical studies, it is clear that the inflammatory responses that occur during the reperfusion phase have an enormous effect on the survival of the cardiomyocytes that survive ischemia. Hausenloy et al., (2015), N Engl J Med 373:1073-1075; Altamirano et al., (2015), if Physiol 595:3773-3788. Although several anti-inflammatory drugs have been developed, so far none have been proven to be effective. It has been well-documented that the recruited monocytes have a biphasic property and that many of the developed drugs aim to target inflammatory activities during the MI phase. However, it was also noticed that some of these anti-inflammatory drugs also affected the resident cardiac macrophages. Unlike the infiltrating monocyte-derived macrophages, the resident cardiac macrophages are primarily derived from embryonic precursors and are more efficient at internalizing debris and engulfing apoptotic cardiomyocytes. Epelman et al., (2014), Immunity 40:91-104. Studies revealed that these cells have important hemostatic roles as inhibition of their inflammatory activities actually prolonged the overall inflammation phase that ultimately resulted in decreased cardiac function. Wan et al., (2013), Circ Res 113:1004-1012.

Accordingly, the PLPs in the present study are likely targeting the newly recruited monocyte-derived macrophages only, as the plain liposome control failed to show any accumulation in the infarcted heart when injected at 72 hours of reperfusion. Thus, the PLPs-CoPPs injected at 72 hours of reperfusion were likely to be phagocytized by their monocyte-turned-macrophage carriers immediately after infiltrating the injured myocardium, rather than being able to freely interact with the resident cardiac macrophages. There have been no reports on the effect of CoPP on resident cardiac macrophages, although the present study showed no significant difference in the therapeutic outcome between the CoPP-treated mice and the PLPs-CoPP-treated mice. Since the number of resident cardiac macrophages is known to be low compared to recruited monocytes-derived macrophages (Luo et al., (2014), Stem Cells Transl Med 3:734-744), it is likely that any significant difference between CoPP and PLPs-CoPP would only be seen at a longer time point. Nevertheless, the present study clearly demonstrated intravenously injection of PLP-CoPP at 72 hours post-infarction could potentially be an excellent strategy for lowering the inflammatory activities of the newly recruited monocytes-derived macrophages while sparing the resident cardiac macrophages.

CoPP has been shown to enhance the expression of transcription factor FOXO1 and facilitate the binding of FOXO1 to the promoter of HO-1, thus increasing the transcriptional activity of HO-1. Liu et al., (2013), PLoS One 8:e80521. Recently, it was demonstrated that pretreatment with CoPP protects human embryonic stem cell-derived cardiomyocytes from I/R injury in both in vitro and in vivo models. Luo et al., (2014), Stem Cells Trnasl Med 3:734-744. Examination of the hearts of a murine model of I/R injury showed the delivery of either CoPP or PLPs–CoPP induced HO-1 expression, as opposed to the mice that were treated with saline or Lipo–CoPP. The increased CoPP-induced HO-1 expression resulted in the downregulation of the expression of several pro-inflammatory genes. Others have shown the HO-1 is a cardioprotective enzyme that either directly or indirectly downregulates the expression of several pro-inflammatory cytokines. Sodhi et al., (2015), J Cardiol Ther 2:291-301; Collino et al., (2013), Dis Model Mech 6:1012-1020; Wang et al., (2010), Circulation 121: 1912-1925.

While many studies have demonstrated the benefits of CoPP in treating I/R injury in various animal models, no human clinical data is available on the efficacy of the drug. One of the key concerns is the cobalt component of CoPP, as it is a heavy metal. Early studies have suggested long-term systemic injection of CoPP could lead to hepatotoxicity; Schmidt, (2007), FASEB J 21:2639. Indeed, in the in vivo study on the cardiac function of a murine model of MI after CoPP treatments showed a significant increase in serum level of ALT, which is the gold standard biomarker for hepatotoxicity. Both AST and TBIL are also being clinically tested for hepatotoxicity. However, unlike ALT, assays for AST and TBIL are only considered as supplementary to support ALT measurement, due to high frequency of discrepancy of either biomarker. Ozer et al., (2008), Toxicology 245:194-205. Even though no significant difference was seen among the CoPP treatment groups in AST and TBIL measurements, the elevated ALT level in the free CoPP treatment group indicated ALT did induce some level of hepatotoxicity. More importantly, neither the Lipo–CoPP nor the PLP–CoPP treatment group showed any significant increase in ALT serum level after the 28-day period. Likewise, free CoPP was shown to induce renal toxicity, as the serum level of BUN and CRE was significantly higher than the other treatment groups. Collectively, although systemically delivered free CoPP was shown to improve the overall cardiac function in a murine model of MI without inducing additional cardiotoxicity, signs of hepatotoxicity and renal toxicity were observed. In contrast, even though PLP–CoPP had a similar level of cardiac improvement, it did not induce any adverse effect on the liver and kidney; thus greatly improving the efficacy of the delivered CoPP.

In sum, the PLPs described in this study utilized only the protein component of human PMPs, and not the membrane phospholipids. Consequently, the PLPs showed low affinity for endothelium in both in vitro and in vivo models, which enhanced their chances of binding to the circulating monocytes that are being recruited during post-myocardial infarction. Thus, PLPs displayed better targeting to the infarcted heart than the plain liposomes via hitchhiking on the circulating monocytes. This minimized the need of relying on the EPR effect as the main route for reaching the heart. Administration of PLPs–CoPP at 72 hours of reperfusion is an excellent therapeutic strategy for lowering cardiac inflammation, as the encapsulated CoPPs are likely to downregulate the inflammatory activity in the recruited monocytes-derived macrophages while sparing the resident cardiac macrophages (FIG. 8). Furthermore, intravenously injected PLP–CoPP exhibited similar levels of cardiac improvement as free CoPP, while reducing the adverse effects of the drug.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kits, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or" as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A proteo-microparticle, comprising a microparticle and a mixture of membrane proteins of resting or partially activated platelets, wherein the mixture of proteins comprises all of CD62, GPIIb, and CD42c, wherein the proteo-microparticle binds circulating blood cells, which are capable of migrating to an injured site; wherein the proteo-microparticle does not bind healthy endothelial cells; wherein the proteo-microparticle encapsulates a therapeutic agent, wherein the proteo-microparticle is a proteoliposome comprising a liposome, and wherein the proteoliposome is substantially free of lipid components of platelet membranes.

2. The proteo-microparticle of claim 1, wherein the circulating blood cells are neutrophils or monocytes.

3. The proteo-microparticle of claim 1, wherein the liposome comprises a phospholipid and cholesterol.

4. The proteo-microparticle of claim 1, wherein the mixture of proteins is free of CD40L or CD18.

5. The proteo-microparticle of claim 1, wherein the mixture of proteins is isolated from partially activated platelets.

6. The proteo-microparticle of claim 1, wherein the mixture of proteins is isolated from resting platelets.

7. The proteo-microparticle of claim 1, wherein the therapeutic agent is a cardioprotective agent.

8. The proteo-microparticle of claim 7, wherein the cardioprotective agent is an anti-inflammatory agent, an anti-apoptotic agent, anti-fibrotic agent, an immuno-modulatory agent, or a proangiogenic agent.

9. A kit for delivering a therapeutic agent, the kit comprising a proteo-microparticle set forth in claim 1.

10. A method for delivering a therapeutic agent to a subject, comprising administering to the subject a proteo-microparticle as set forth in claim 1.

11. The method of claim 10, wherein the subject is a human patient having, suspected of having, or at risk for an ischemic heart disease.

12. A method for treating an ischemic heart disease, comprising administering to a subject in need thereof an effective amount of the proteo-microparticle set forth in claim 1, wherein the therapeutic agent is for treating the ischemic heart disease.

* * * * *